United States Patent
Mathur et al.

(10) Patent No.: US 11,491,124 B2
(45) Date of Patent: Nov. 8, 2022

(54) PYRETHROID SPRAY FORMULATIONS AND METHODS OF USING THE SAME

(71) Applicant: Contract Pharmaceuticals Limited, Mississauga (CA)

(72) Inventors: Rajiv Mathur, Mississauga (CA); Mallika Tushakiran, Mississauga (CA); Nidhi Parikh, Brampton (CA)

(73) Assignee: Contract Pharmaceuticals Limited, Mississauga (CA)

( * ) Notice: Subject to any disclaimer, the term of this patent is extended or adjusted under 35 U.S.C. 154(b) by 0 days.

(21) Appl. No.: 16/335,832

(22) PCT Filed: Dec. 12, 2017

(86) PCT No.: PCT/CA2017/051505
§ 371 (c)(1),
(2) Date: Mar. 22, 2019

(87) PCT Pub. No.: WO2018/107284
PCT Pub. Date: Jun. 21, 2018

(65) Prior Publication Data
US 2020/0022934 A1    Jan. 23, 2020

Related U.S. Application Data

(60) Provisional application No. 62/433,139, filed on Dec. 12, 2016.

(51) Int. Cl.
| | | |
|---|---|---|
| *A61K 31/192* | (2006.01) | |
| *A61M 11/00* | (2006.01) | |
| *A61K 9/00* | (2006.01) | |
| *A61K 9/12* | (2006.01) | |
| *A61K 9/14* | (2006.01) | |
| *A61K 31/05* | (2006.01) | |
| *A61K 47/02* | (2006.01) | |
| *A61K 47/10* | (2017.01) | |
| *A61K 47/12* | (2006.01) | |
| *A61K 47/32* | (2006.01) | |
| *A61K 47/34* | (2017.01) | |
| *A61K 47/44* | (2017.01) | |
| *A61M 11/02* | (2006.01) | |
| *A61M 35/00* | (2006.01) | |

(52) U.S. Cl.
CPC .......... *A61K 31/192* (2013.01); *A61K 9/0014* (2013.01); *A61K 9/124* (2013.01); *A61K 9/14* (2013.01); *A61K 31/05* (2013.01); *A61K 47/02* (2013.01); *A61K 47/10* (2013.01); *A61K 47/12* (2013.01); *A61K 47/32* (2013.01); *A61K 47/34* (2013.01); *A61K 47/44* (2013.01); *A61M 11/001* (2014.02); *A61M 11/02* (2013.01); *A61M 35/00* (2013.01)

(58) Field of Classification Search
CPC .... A61K 31/192; A61K 9/0014; A61K 9/124; A61K 9/14; A61K 31/05; A61K 47/02; A61K 47/10; A61K 47/12; A61K 47/32; A61K 47/34; A61K 47/44; A61K 31/277; A61K 9/12; A61K 31/215; A61M 11/001; A61M 11/02; A61M 35/00; A01N 53/00; A61P 33/14
See application file for complete search history.

(56) References Cited

U.S. PATENT DOCUMENTS

| | | | |
|---|---|---|---|
| 4,607,050 A * | 8/1986 | Kieran | A01N 25/06 514/520 |
| 5,292,504 A | 3/1994 | Cardin et al. | |
| 8,119,150 B2 | 2/2012 | Tamarkin et al. | |
| 8,486,374 B2 | 7/2013 | Tamarkin et al. | |
| 2007/0020304 A1 | 1/2007 | Tamarkin et al. | |
| 2012/0148503 A1* | 6/2012 | Tamarkin | A01N 53/00 424/43 |

(Continued)

FOREIGN PATENT DOCUMENTS

| | | |
|---|---|---|
| AU | 8964482 A | 4/1983 |
| WO | WO-2000/054586 A1 | 9/2000 |

(Continued)

OTHER PUBLICATIONS

Bufo, et al., "Industry perspective Packaging/Dispensing Technology. Bag-on-valve (BOV) technology in cosmedic products," Household and Personal Care TODAY, Feb. 2011, pp. 34-36.

(Continued)

*Primary Examiner* — Snigdha Maewall
(74) *Attorney, Agent, or Firm* — Goodwin Procter LLP

(57) ABSTRACT

Sprayable compositions comprising a pyrethroid, a viscosity building agent, an emulsifier or surfactant, and an emollient are provided. The compositions have a viscosity that allows for delivery of the spray from a pressurized container such that the pyrethroid is administered in a consistent amount that uniformly covers the body of a subject. This obviates the need to rub the composition into the skin. In preferred embodiments, the pyrethroid is permethrin; the viscosity building agent is selected from the group consisting of carbomers, xanthan gum, or a combination thereof; the emulsifier or surfactant is selected from the group consisting of glyceryl mononstearate, PEG40 hydrogenated castor oil, cholesterol, steareth-10, steareth-20, and combinations thereof; and the emollient is selected from the group consisting of C12-C15 alkyl benzoates, diisopropyl adipate, silicon oil, mineral oil, or any combination thereof.

18 Claims, No Drawings

(56) References Cited

U.S. PATENT DOCUMENTS

2014/0187424 A1* 7/2014 Norton ................. A01N 57/20
504/101

FOREIGN PATENT DOCUMENTS

| WO | WO-2000/072821 A1 | 12/2000 |
|----|-------------------|---------|
| WO | WO-2002/062326 A1 | 8/2002  |
| WO | WO-2004/037225 A2 | 5/2004  |
| WO | WO-2008/098168 A2 | 8/2008  |
| WO | WO-2011/138678 A2 | 11/2011 |

OTHER PUBLICATIONS

Extended European Search Report for EP17880680.8 dated Jul. 29, 2020 (9 pgs.).
International Search Report for PCT/CA2017/051505, dated Mar. 21, 2018 (5 pages).
Written Opinion for PCT/CA2017/051505, dated Mar. 21, 2018 (6 pages).
Mandate et al., "Liquids' atomization with two different nozzles: Modeling of the effects of some processing and formulation conditions by dimensional analysis," Powder Technology (2012) 224: 323-330.

* cited by examiner

PYRETHROID SPRAY FORMULATIONS AND METHODS OF USING THE SAME

CROSS-REFERENCE TO RELATED APPLICATIONS

This application is the national stage of International (PCT) Patent Application Serial No. PCT/CA2017/051505, filed Dec. 12, 2017, which claims the benefit of and priority to U.S. provisional patent application Ser. No. 62/433,139 filed Dec. 12, 2016, the contents of each of which are hereby incorporated by reference hereby in its entirety.

FIELD

The present disclosure relates to sprayable pyrethroid-containing compositions, spray devices comprising the pyrethroid-containing compositions, and methods for treating an arthropod infestation using the compositions.

BACKGROUND

Certain chrysanthemum flowers produce active insecticidal compounds called pyrethrins, which can be extracted from the flower with organic solvents. Pyrethroids are synthetic chemicals that have a similar structure to, and can be derived from, pyrethrins. Pyrethroids are particularly toxic to invertebrates, such as arthropods, arachnids, and myriapods. Pyrethroids are relatively non-toxic to mammals, including humans, and are susceptible to sunlight degradation. These features make pyrethroids desirable agents for treating arthropod infestations.

Permethrin is, perhaps, the best known pyrethroid, and is often used as an insecticide, aracide, and/or repellant. It functions as a neurotoxin affecting the neuron membrane by prolonging activation of the sodium channel. Permethrin is not known to harm most mammals or birds. It has a low mammalian toxicity and is poorly absorbed by the skin.

Topically applied permethrin is used to treat scabies (mites [*Sarcoptes scabiei*] that attach to the skin) in adults and children over the age of 2 months. Over-the-counter permethrin, sold under the brand name Nix® is also used to treat head lice (*Pediculus humanus* capitis) in adults and children.

Permethrin is currently available for topical use as a prescription cream under the tradename Elimite®. To treat scabies, subjects apply a thin layer of the cream over the entire body, from the head to the soles of the feet. This may consume up an entire package of 60 g permethrin cream (although only 30 g should be applied), given that the cream is thick and may be difficult to effectively spread to hard-to-reach places on the body. As a result, patient compliance, and resultant efficacy, can be an issue.

U.S. Pat. No. 8,119,150 describes topical 1% and 5% permethrin foams to treat head lice and scabies.

U.S. Pat. No. 8,486,374 describes waterless compositions comprising insecticides, including permethrin, which are effective to kill insects.

SUMMARY

The present invention provides a propellant-free sprayable pharmaceutical composition of a pyrethroid, which has a viscosity that allows delivery of the composition from a pressurized delivery container (e.g., Bag-on-Valve (BoV)) such that a consistent amount of the pyrethroid is released from the container to easily and uniformly cover the body of a subject with an effective amount of the pyrethroid. Furthermore, the pyrethroid is released from the container in spray particles having a particle size to facilitate uniform coverage of the body of a subject (e.g., a human subject) while minimizing inhalation by the subject.

The consistency of the sprayable pharmaceutical composition allows uniform delivery of a desired dose (e.g., by releasing a "fine mist pattern" with uniform particles/droplets in a continuous spraying fashion capable of covering a large surface area, e.g., the surface area of the body of a subject) of the pyrethroid (e.g., permethrin), which obviates the need to massage thick cream over the body of the subject, which enhances uniform and consistent delivery and patient compliance.

The sprayable pyrethroid compositions disclosed herein facilitate more effective and uniform delivery while having an elegant, aesthetic feel. They can be sprayed quickly and evenly over the entire body surface area and may be massaged into the skin for thorough and complete coverage and minimal oily feel. Thus, the sprayable composition of a pyrethroid of the present invention represents a substantial improvement with respect to patient compliance and efficacy over currently available therapies for treating conditions such as scabies.

Accordingly, in one aspect, the invention provides a sprayable composition that includes a pyrethroid; a viscosity building agent; an emulsifier/surfactant; and an emollient. In certain embodiments, the sprayable composition further comprises a preservative; an antioxidant; a humectant; a pH adjustment agent; and/or a vehicle. In certain embodiments, the sprayable composition of the present invention is a pharmaceutical composition.

In certain embodiments, the sprayable composition of pyrethroid, e.g., permethrin, includes an emollient selected from $C_{12}$-$C_{15}$ alkyl benzoate, diisopropyl adipate, silicon oil, mineral oil, and any combination(s) thereof. In certain embodiments, the sprayable composition of pyrethroid, e.g., permethrin, includes a viscosity building agent selected from carbomer and xanthan gum. In certain embodiments, the sprayable composition of pyrethroid, e.g., permethrin, includes an emulsifier/surfactant selected from glyceryl monostearate, cholesterol, steareth-10, steareth-20, polyethylene glycol 40 hydogenated castor oil, and any combination(s) thereof. In certain embodiments, the sprayable composition of pyrethroid, e.g., permethrin, includes a preservative selected from methyl paraben and propyl paraben. In certain embodiments, the sprayable composition of pyrethroid, e.g., permethrin, includes a humectant selected from propylene glycol and glycerin. In certain embodiments, the sprayable composition of pyrethroid, e.g., permethrin, includes sodium hydroxide as a pH adjusting agent. In certain embodiments, the sprayable composition of pyrethroid, e.g., permethrin, includes water as a vehicle. In certain embodiments, the sprayable composition of pyrethroid, e.g., permethrin, includes butylated hydroxytoluene as an antioxidant.

In certain embodiments, the sprayable composition of pyrethroid, e.g., permethrin, includes emollients diisopropyl adipate, mineral oil, and/or silicone oil; emulsifiers/surfactants glyceryl monostearate, cholesterol, steareth-10, and/or PEG40 hydogenated castor oil; humectant propylene glycol; and viscosity building agent carbomer and xanthan gum. In certain embodiments, the sprayable composition of pyrethroid, e.g., permethrin, includes emollients diisopropyl adipate, mineral oil, and/or silicone oil; emulsifiers/surfactants glyceryl monostearate, and/or PEG40 hydogenated castor oil; humectant glycerin; and viscosity building agent carbomer.

In certain embodiments of any of the foregoing compositions, the composition comprises: between about 0.1% and about 0.3% by weight of the viscosity building agent; between about 10% and about 25% by weight of the emollient; between about 1% and about 10% by weight of the emulsifier/surfactant; between about 0.5% and about 20% by weight of the humectant; between about 0.01% and about 1.2% by weight of the preservative; between about 0.01% and about 0.5% by weight of the anti-oxidant; between about 30% and about 75% of the vehicle; and/or between about 0.01% and about 1.0% by weight of the pH-adjustment agent.

In certain embodiments, the composition includes between about 0.1% and about 30% by weight diisopropyl adipate (e.g., between about 0.5% and about 10% by weight diisopropyl adipate), between about 0.1% and about 60% by weight silicon oil (e.g., between about 0.5% and about 10% by weight silicon oil), and/or between about 0.1% and about 60% by weight mineral oil (e.g., between about 0.5% and about 60% by weight mineral oil).

In another aspect, the invention provides a sprayable composition comprising: a pyrethroid; a viscosity building agent; about 0.1% to about 60% by weight silicon oil; about 0.1 to about 30% by weight diisopropyl adipate; and at least 40% by weight water, wherein the ratio of silicon oil to diisopropyl adipate is between about 10:1 and about 1:20.

In certain embodiments of any of the foregoing compositions, the emollient is a combination of diisopropyl adipate, silicon oil, and mineral oil. In certain embodiments, the ratio of silicon oil to diisopropyl adipate is between about 10:1 and about 1:20, e.g., between about 1:1 and about 1:10, e.g., 1:1, 1:5, or 1:10.

In another aspect, the invention provides a sprayable composition comprising: a pyrethroid; a viscosity building agent; about 0.1% to about 60% by weight silicon oil; about 0.1 to about 20% by weight $C_{12}$-$C_{15}$ alkyl benzoate; and at least 40% by weight water, wherein the ratio of silicon oil to $C_{12}$-$C_{15}$ alkyl benzoate is between about 10:1 and about 1:20.

In certain embodiments, the composition comprises between about 5% and about 15% by weight $C_{12}$-$C_{15}$ alkyl benzoate. In certain embodiments, the composition comprises between about 0.5% and about 10% by weight silicon oil. In certain embodiments, the composition comprises about 5% by weight of the pyrethroid; between 0.5% and about 10% by weight silicon oil; and between about 5% and about 10% by weight $C_{12}$-$C_{15}$ alkyl benzoate. In certain embodiments, the ratio of silicon oil to $C_{12}$-$C_{15}$ alkyl benzoate is between about 10:1 and about 1:20, e.g., between about 1:1 and about 1:10, e.g., 1:1, 1:5, or 1:10.

In certain embodiments of any of the foregoing compositions, the silicon oil is a volatile silicon oil, e.g., cyclomethicone.

In certain embodiments of any of the foregoing compositions, the pyrethroid active agent is selected from allethrin, bifenthrin, cyfluthrin, cypermethrin, cyphenothrin, deltamethrin, esfenvalerate, etofenprox, fenpropathrin, fenvalerate, flucythrinate, flumenthrin, imiprothrin, λ-cychalothrin, metofluthrin, permethrin, prallethrin, resmethrin, silafluofen, sumithrin, τ-fluvalinate, tefluthrin, tetramethrin, tralomethrin, and transfluthrin. In certain embodiments, the pyrethroid is permethrin. For example, the composition may comprise up to about 7.5% by weight of active agent, e.g., permethrin, e.g., between about 2.5% and about 7.5% by weight of active agent, e.g., permethrin, e.g., about 5% by weight of active agent, e.g., permethrin.

In certain embodiments of any of the foregoing compositions, the composition includes between about .005% and about 1%, e.g., between about 0.1% and about 0.3%, by weight of the viscosity building agent. In certain embodiments, the composition comprises a carbomer, xanthan gum, or a combination thereof. In certain embodiments, the composition comprises between about 0.01% and about 3.0% by weight of the carbomer and/or between about 0.005% and about 3.0% by weight xanthan gum. In certain embodiments, the viscosity building agent is a carbomer. In certain embodiments, the viscosity building agent is a combination of a carbomer and xanthan gum.

In certain embodiments, the composition further includes an emulsifier/surfactant. In certain embodiments of any of the foregoing compositions, the emulsifier/surfactant is selected from glyceryl monostearate, PEG40 hydrogenated castor oil, POE20 cetyl ether, or any combination thereof. In certain embodiments, the emulsifier/surfactant comprises glycerol monostearate, PEG40 hydrogenated castor oil, cholesterol, steareth-10, steareth-20, or any combination thereof. In certain embodiments, the composition comprises between about 0.5% and about 10% glycerol monostearate, between about 0.1% and about 5% PEG40 hydrogenated castor oil, between about 0.1% and about 5% cholesterol, between about 0.1% and about 5% steareth-10, and/or between about 0.1% and about 5% steareth-20. In certain embodiments, the emulsifier/surfactant is a combination of glycerol monostearate, PEG40 hydrogenated castor oil, cholesterol, and steareth-10. In certain embodiments, the emulsifier/surfactant is a combination of glycerol monostearate, and PEG40 hydrogenated castor oil.

In certain embodiments of any of the foregoing compositions, the composition does not comprise PEG200, PEG400, isopropyl myristate, lanolin alcohols, coconut oils, POE2 cetyl ether, formaldehyde, or combinations thereof. In certain embodiments, the composition further comprises piperonyl butoxide.

In certain embodiments of any of the foregoing compositions, the composition further comprises a preservative, for example, methyl paraben, propyl paraben, or a combination thereof. In certain embodiments, the composition comprises between about 0.02% and about 0.3% by weight methyl paraben and/or between about 0.01% and about 0.3% by weight propyl paraben.

In certain embodiments of any of the foregoing compositions, the composition further comprises a humectant, for example, propylene glycol, glycerin, or a combination thereof. In certain embodiments, the composition comprises between about 0.5% and about 10% by weight propylene glycol and/or between about 0.5% and about 10% by weight glycerin. In certain embodiments, the humectant is propylene glycol. In certain embodiments, the humectant is glycerin.

In certain embodiments of any of the foregoing compositions, the composition further comprises an antioxidant, for example, butylated hydroxytoluene. For example, in certain embodiments, the composition comprises between about 0.01% and about 0.5% by weight butylated hydroxytoluene.

In certain embodiments of any of the foregoing compositions, the composition further comprises a pH-adjustment agent, for example, sodium hydroxide. For example, in certain embodiments, the composition comprises between about 0.01% and about 3.0% by weight sodium hydroxide. In certain embodiments, the amount of sodium hydroxide and, therefore, the final amount of purified water can vary from batch-to-batch, as would be understood by a person of ordinary skill in the art. The amount of sodium hydroxide may vary depending upon the adjusted pH required. The amount of water may also vary and can be added to achieve a final concentration of 100% by weight for each final composition.

In certain embodiments of any of the foregoing compositions, the composition further comprises an anti-itch medication.

In certain embodiments of any of the foregoing compositions, the composition has a viscosity of between about 1,000 cPs and about 32,000 cPs, e.g., between about 2,000 cPs and about 32,000 cPs. In certain embodiments, the composition has a pH between about 4.5 and about 7.5.

In certain embodiments of the foregoing compositions, the pyrethroid is permethrin; the viscosity building agent is a combination of a carbomer and xanthan gum; the emulsifier/surfactant is a combination of glycerol monostearate, PEG40 hydrogenated castor oil, cholesterol, and steareth-10; and the emollient is a combination of diisopropyl adipate, silicon oil, and mineral oil. In certain embodiments of the foregoing compositions, the pyrethroid is permethrin; the viscosity building agent is a combination of a carbomer and xanthan gum; the emulsifier/surfactant is a combination of glycerol monostearate, PEG40 hydrogenated castor oil, cholesterol, and steareth-10; the emollient is a combination of diisopropyl adipate, silicon oil, and mineral oil; the preservative is a combination of methyl paraben and propyl paraben; the humectant is propylene glycol; and the antioxidant is butylated hydroxytoluene.

In certain embodiments of the foregoing compositions, the pyrethroid is permethrin; the viscosity building agent is a carbomer; the emulsifier/surfactant is a combination of glycerol monostearate and PEG40 hydrogenated castor oil; and the emollient is a combination of diisopropyl adipate, silicon oil, and mineral oil. In certain embodiments of the foregoing compositions, the pyrethroid is permethrin; the viscosity building agent is a carbomer; the emulsifier/surfactant is a combination of glycerol monostearate and PEG40 hydrogenated castor oil; the emollient is a combination of diisopropyl adipate, silicon oil, and mineral oil; the preservative is a combination of methyl paraben and propyl paraben; the humectant is glycerin; and the antioxidant is butylated hydroxytoluene.

In certain embodiments of the foregoing compositions, the invention provides a sprayable composition comprising, by weight: about 5% permethrin; between about 0.01% and about 2.0% of a carbomer; between about 0.005% and about 3.0% xanthan gum; between about 0.5% and about 10% glycerol monostearate; between about 0.1% and about 5% PEG40 hydrogenated castor oil; between about 0.1% and about 5% cholesterol; between about 0.1% and about 5% steareth-10; between about 0.1% and about 30% diisopropyl adipate; between about 0.1% and about 60% silicon oil; and between about 0.1% and about 60% mineral oil. In certain embodiments, the composition further comprises: between about 0.02% and about 0.3% methyl paraben; between about 0.01% and about 0.3% propyl paraben; between about 0.5% and about 10% propylene glycol; and/or between about 0.01% and 0.5% butylated hydroxytoluene.

In certain embodiments of the foregoing compositions, the invention provides a sprayable composition comprising, by weight: about 5% permethrin; between about 0.01% and about 2.0% of a carbomer; between about 0.5% and about 10% glycerol monostearate; between about 0.1% and about 5% PEG40 hydrogenated castor oil; between about 0.1% and about 30% diisopropyl adipate; between about 0.1% and about 60% silicon oil; and between about 0.1% and about 20% mineral oil. In certain embodiments, the composition further comprises: between about 0.02% and about 0.3% methyl paraben; between about 0.01% and about 0.3% propyl paraben; between about 0.5% and 10% glycerin; and/or between about 0.01% and about 0.5% butylated hydroxytoluene.

In certain embodiments of any of the foregoing compositions, the composition does not comprise a propellant.

In another aspect, the invention provides a composition comprising a pyrethroid, e.g., permethrin, a viscosity building agent, silicon oil, $C_{12}$-$C_{15}$ alkyl benzoate, and at least 40%, by weight, water. In certain embodiments, the composition comprises between about 0.1% and about 60% by weight silicon oil. In certain embodiments, the composition comprises between about 2% and about 20% by weight $C_{12}$-$C_{15}$ alkyl benzoate. In certain embodiments, the ratio of silicon oil to $C_{12}$-$C_{15}$ alkyl benzoate is between about 10:1 and about 1:20. In certain embodiments, the viscosity building agent is selected from a carbomer, xanthan gum and a combination thereof. In certain embodiments, the composition comprises about 5% by weight of the pyrethroid, e.g., permethrin. In certain embodiments, the silicon oil is a volatile silicon oil, e.g., cyclomethicone.

In another aspect, the invention provides a composition comprising a pyrethroid, e.g., permethrin, a viscosity building agent, silicon oil, diisopropyl adipate, and at least 40%, by weight, water. In certain embodiments, the composition comprises between about 0.1% and about 60% by weight silicon oil. In certain embodiments, the composition comprises between about 2% and about 20% by weight diisopropyl adipate. In certain embodiments, the ratio of silicon oil to diisopropyl adipate is between about 10:1 and about 1:20. In certain embodiments, the viscosity building agent is selected from a carbomer, xanthan gum and a combination thereof. In certain embodiments, the composition comprises about 5% by weight of the pyrethroid, e.g., permethrin. In certain embodiments, the silicon oil is a volatile silicon oil, e.g., cyclomethicone.

In another aspect, the invention provides a unit dosage form comprising from about 25 grams to about 35 grams, e.g., about 30 grams, of any of the foregoing compositions.

In another aspect, the invention provides a method for treating an infestation of an arthropod in a subject in need thereof. The method comprises topically administering to the subject a therapeutically effective amount of any of the foregoing compositions. In certain embodiments, the arthropod is *Sarcoptes scabiei* or *Pediculus humanus capitis*. In certain embodiments, the subject is a human. In certain embodiments, the therapeutically effective amount of the composition is 30 grams.

In another aspect, the invention provides a Bag-on-Valve (BoV) aerosol system comprising an aerosol valve and an attached bag containing any of the foregoing compositions. In certain embodiments, the bag is a laminated aluminum bag. In certain embodiments, the system further comprises a propellant, e.g., compressed air or nitrogen. In certain embodiments, the system further comprises an actuator. In certain embodiments, the system further comprises a can, aluminum plate, or tin plate. In certain embodiments, the system further comprises an overcap. In certain embodiments, the pressure in the system, for example, between the inner wall of the container and the outer surface of the composition-containing bag, is between about 100 psi and about 130 psi. In certain embodiments, the composition has a mean particle diameter of about 5 μm to about 100 μm, e.g., about 5 μm to about 90 μm when sprayed from the BoV system. In certain embodiments, the composition has a mean particle diameter of equal to or less than about 90 µm when sprayed from the BoV system. In certain embodiments, the composition has a mean particle diameter of about 5 µm, about 10 µm, about 20 µm, about 25 µm, about 30 µm, about 35 µm, about 40 µm, about 50 µm, about 60 µm, about 70 µm, about 80 µm, or about 90 µm when sprayed from the BoV system.

Various aspects and embodiments of the invention are described in more detail below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise.

DETAILED DESCRIPTION

The present invention provides a propellant-free sprayable pharmaceutical composition of a pyrethroid, which has a viscosity that allows delivery of the composition from a pressurized delivery container (e.g., Bag-on-Valve (BoV)) such that a consistent amount of the pyrethroid is released from the container to easily and uniformly cover the body of a subject with an effective amount of the pyrethroid. Furthermore, the pyrethroid is released from the container in spray particles having a particle size to facilitate uniform coverage of the body of a subject (e.g., a human subject) while minimizing inhalation by the subject.

The consistency of the sprayable pharmaceutical composition allows uniform delivery of a desired dose (e.g., by releasing a "fine mist pattern" with uniform particles/droplets in a continuous spraying fashion capable of covering a large surface area, e.g., the surface area of the body of a subject) of the pyrethroid (e.g., permethrin), which obviates the need to massage thick cream over the body of the subject, which enhances uniform and consistent delivery and patient compliance.

The sprayable pyrethroid compositions disclosed herein facilitate more effective and uniform delivery while having an elegant, aesthetic feel. They can be sprayed quickly and evenly over the entire body surface area and may be massaged into the skin for thorough and complete coverage and minimal oily feel. Thus, the sprayable composition of a pyrethroid of the present invention represents a substantial improvement with respect to patient compliance and efficacy over currently available therapies for treating conditions such as scabies.

A. Definitions

The term "pyrethroid" means a compound which is similar to compounds, such as pyrethrins, which are produced by pyrethrum flowers, such as *Chrysanthemum cinerariaefolium* and *Chyrsanthemum coccineum*. The pyrethroid may be derived from chrysanthemic acid, such as by altering the alcohol group of the ester of the acid. Examples of a pyrethroid include allethrin, bifenthrin, cyfluthrin, cypermethrin, cyphenothrin, deltamethrin, esfenvalerate, etofenprox, fenpropathrin, fenvalerate, flucythrinate, flumenthrin, imiprothrin, λ-cychalothrin, metofluthrin, permethrin, prallethrin, resmethrin, silafluofen, sumithrin, τ-fluvalinate, tefluthrin, tetramethrin, tralomethrin, and transfluthrin.

The term "treat" (and corresponding terms "treatment" and "treating") includes palliative, restorative, and preventative treatment of a subject. The term "palliative treatment" refers to treatment that eases or reduces the effect or intensity of a condition in a subject without curing the condition. The term "preventative treatment" (and the corresponding term "prophylactic treatment") refers to treatment that prevents the occurrence of a condition in a subject. The term "restorative treatment" refers to treatment that halts the progression of, reduces the pathologic manifestations of, or entirely eliminates a condition in a subject.

The term "therapeutically effective amount" refers to an amount of an active agent that, when administered to a subject for treating a disease, is sufficient to effect treatment for the disease. "Therapeutically effective amount" can vary depending on the compound, the disease and its severity, the age, the weight, etc. of the subject to be treated.

The term "spray device" refers to any device which is capable of ejecting a volume of a composition in the form of a spray. It may include an operating mechanism (e.g., a spray head or pump) attached to a fluid reservoir. The spray device may be manual or pressurized. In one embodiment, the spray device utilizes bag-on-valve technology.

The term "arthropod" refers to invertebrate animals with an exoskeleton, a segmented body, and jointed appendages which belong to the phylum Arthopoda. The term includes, but does not exclude, insects (e.g., mosquitos, cockroaches, and ants), arachnids (e.g., spiders, mites, and ticks), and myriapods (e.g., centipedes and millipedes).

As used herein, the terms "subject" and "patient" are used interchangeably and refer to an organism to be treated by the methods and compositions of the present invention. Such organisms may be a mammal (e.g., human, mouse, rat, guinea pig, dog, cat, horse, cow, pig, or non-human primate, such as a monkey, chimpanzee, baboon, and rhesus). In certain embodiments, the subject is a human.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see Martin, Remington's Pharmaceutical Sciences, 15th Ed., Mack Publ. Co., Easton, Pa. (1975).

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

Unless defined otherwise, all technical and scientific terms used herein have the same meaning as commonly understood by one of ordinary skill in the art to which this invention belongs.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also include the specific quantitative value itself, unless specifically stated otherwise. As used herein, the term "about" refers to a ±10% variation from the nominal value unless otherwise indicated or inferred.

Where a molecular weight is provided and not an absolute value, for example, of a polymer, then the molecular weight should be understood to be an average molecule weight, unless otherwise stated or understood from the context.

It should be understood that the order of steps or order for performing certain actions is immaterial so long as the present invention remains operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

As a general matter, compositions specifying a percentage are by weight unless otherwise specified. Further, if a variable is not accompanied by a definition, then the previous definition of the variable controls.

B. Pharmaceutical Compositions

In one aspect, the invention provides a sprayable composition comprising: a pyrethroid; a viscosity building agent; an emulsifier/surfactant; and an emollient.

Accordingly, in one aspect, the invention provides a sprayable composition that includes a pyrethroid; a viscosity building agent; an emulsifier/surfactant; and an emollient. In certain embodiments, the sprayable composition further comprises: a preservative; an antioxidant; a humectant; a pH adjustment agent; and/or a vehicle. In certain embodiments, the sprayable composition of the present invention is a pharmaceutical composition.

In certain embodiments, the sprayable composition of pyrethroid includes an emollient selected from $C_{12}$-$C_{15}$ alkyl benzoate, diisopropyl adipate, silicon oil, mineral oil, and any combination(s) thereof. In certain embodiments, the sprayable composition of pyrethroid includes a viscosity building agent selected from carbomer. xanthan gum, and any combination(s) thereof. In certain embodiments, the sprayable composition of pyrethroid includes an emulsifier/surfactant selected from glyceryl monostearate, cholesterol, steareth-10, steareth-20, polyethylene glycol 40 hydogenated castor oil, and any combination(s) thereof. In certain embodiments, the sprayable composition of pyrethroid includes a preservative selected from methyl paraben, propyl paraben, and any combination(s) thereof. In certain embodiments, the sprayable composition includes a humectant selected from propylene glycol and glycerin. In certain embodiments, the sprayable composition of pyrethroid includes sodium hydroxide as a pH adjusting agent. In certain embodiments, the sprayable composition of pyrethroid includes water as a vehicle. In certain embodiments, the sprayable composition of pyrethroid, e.g., permethrin, includes butylated hydroxytoluene as an antioxidant.

In certain embodiments, the sprayable composition of pyrethroid includes emollients diisopropyl adipate, mineral oil, and/or silicone oil; emulsifiers/surfactants glyceryl monostearate, cholesterol, steareth-10, and/or PEG40 hydrogenated castor oil; humectant propylene glycol; and viscosity building agents carbomer and xanthan gum. In certain embodiments, the sprayable composition of pyrethroid includes emollients diisopropyl adipate, mineral oil, and/or silicone oil; emulsifiers/surfactants glyceryl monostearate and/or PEG40 hydrogenated castor oil; humectant glycerin, and viscosity building agent carbomer.

In another aspect, the invention provides a sprayable pharmaceutical composition that includes a pyrethroid; a viscosity building agent; two or more emollients, e.g., silicone oil, $C_{12}$-$C_{15}$ alkyl benzoate and/or diisopropyl adipate, in an amount of about 0.1% to about 60% by weight silicon oil, about 0.1 to about 30% by weight $C_{12}$-$C_{15}$ alkyl benzoate and/or diisopropyl adipate; and at least 40% by weight water, in which the ratio of silicon oil to $C_{12}$-$C_{15}$ alkyl benzoate or diisopropyl adipate may be between about 10:1 and about 1:20.

In certain embodiments, a composition of the invention includes at least 40% by weight water. For example, the composition may include at least about 50%, at least about 60%, or at least about 70%, by weight water. In certain embodiments, the composition includes about 68%, about 69%, about 70%, about 71%, about 72%, about 73%, or about 74% by weight water. In certain embodiments, the composition includes about 70% or about 74% by weight water.

In certain embodiments, a composition of the invention includes one or more additional therapeutic agents. In certain embodiments, the composition further includes piperonyl butoxide. Piperonyl butoxide is an organic compound with no pesticidal activity itself but that enhances the potency of pyrethroids (e.g., permethrin) and pyrethrins. In certain embodiments, the composition further includes an anti-itch medication.

In certain embodiments, the composition does not include PEG200, PEG400, isopropyl myristate, lanolin alcohols, coconut oils, POE2 cetyl ether, formaldehyde, or combinations thereof.

In a certain embodiments, the viscosity of the composition is between about 500 cPs and about 32,000 cPs. In certain embodiments, the viscosity of the composition is between about 5,000 cPs and about 32,000 cPs, e.g., between about 2,000 cPs and about 32,000 cPs, between about 2,000 cPs and about 30,000 cPs, between about 2,000 cPs and about 25,000 cPs, between about 2,000 cPs and about 20,000 cPs, between about 2,000 cPs and about 15,000 cPs, between about 2,000 cPs and about 10,000 cPs, between about 2,000 cPs and about 5,000 cPs, between about 2,250 cPs and about 32,000 cPs, between about 2,500 cPs and about 32,000 cPs, between about 2,750 cPs and about 32,000 cPs, between about 2,000 cPs and about 2,750 cPs, between about 2,250 cPs and about 2,750 cPs, between about 2,500 cPs and about 2,750 cPs, between about 2,000 cPs and about 2,500 cPs, between about 2,250 cPs and about 2,500, between about 2,000 cPs and about 2,250 cPs, about 2,000 cPs, about 2,250 cPs, about 2,500 cPs, about 2,750 cPs, about 3,000 cPs, about 10,000 cPs, about 15,000 cPs, about 20,000 cPs, about 25,000 cPs, about 30,000 cPs, or about 32,000 cPs. In certain embodiments, the composition has a viscosity between about 2,000 cPs and about 32,000 cPs. In certain embodiments, viscosity of the composition can be measured with various instruments known in the art, e.g., a Brookfield viscometer.

In certain embodiments, a composition of the invention has a pH between about 4.5 and about 7.5, e.g., between about 4.5 and about 7.5, between about 5.0 and about 7.5, between about 5.5 and about 7.5, between about 6.0 and about 7.5, between about 6.5 and about 7.5, between about 7.0 and about 7.5, between about 4.5 and about 7.0, between about 5.0 and about 7.0, between about 5.5 and about 7.0, between about 6.0 and about 7.0, between about 6.5 and about 7.0, between about 7.0 and about 7.0, between about 4.5 and about 6.5, between about 5.0 and about 6.5, between about 5.5 and about 6.5, between about 6.0 and about 6.5, between about 4.5 and about 6.0, between about 5.0 and about 6.0, between about 5.5 and about 6.0, about 4.5, about 5.0, about 5.5, about 6.5, about 7.0, or about 7.5. The viscosity of the composition can be measured with various instruments known in the art.

In certain embodiments, a composition of the invention does not contain or comprise a propellant. As used herein, propellant refers to volatile organic compounds ("VOC"). For example, in certain embodiments, a composition of the invention does not comprise volatile organic compounds. Traditional aerosol cans are designed to mix the propellant (volatile organic compounds) with the composition contained in the can. When the composition with VOC is expelled from the container the VOC evaporates and the composition is deposited at the site of application. However, in the BOV the propellant is not a VOC and is not in contact with the product. The propellant is comprised of compressed air/nitrogen, filled in the space between the bag and can. The propellant in this case is not expelled out of the can.

Pyrethroid

In certain embodiments, a composition of the invention includes a pyrethroid. The pyrethroid may be derived from chrysanthemic acid, or may not be derived from chysanthemic acid. Exemplary pyrethroids include allethrin, bifenthrin, cyfluthrin, cypermethrin, cyphenothrin, deltamethrin, esfenvalerate, etofenprox, fenpropathrin, fenvalerate, flucythrinate, flumenthrin, imiprothrin, λ-cychalothrin, metofluthrin, permethrin, prallethrin, resmethrin, silafluofen, sumithrin, τ-fluvalinate, tefluthrin, tetramethrin, tralomethrin, transfluthrin, and combinations thereof. In certain embodiments, the pyrethroid is permethrin.

In certain embodiments, the pyrethroid, e.g., permethrin, is present in the sprayable composition at a therapeutically effective dose. The amount of the pyrethroid can be determined or controlled by a person having ordinary skill in the art.

In certain embodiments, a composition of the invention includes from about 1% to about 10% by weight of the pyrethroid, e.g., permethrin. For example, a composition may include from about 1% to about 10%, from about 1% to about 8%, from about 1% to about 6%, from about 1% to about 4%, from about 1% to about 2%, from about 2% to about 10%, from about 2% to about 8%, from about 2% to about 6%, from about 2% to about 4%, from about 4% to about 10%, from about 4% to about 8%, from about 4% to about 6%, from about 6% to about 10%, from about 6% to about 8%, or from about 8% to about 10% by weight of the pyrethroid, e.g., permethrin. In certain embodiments, the composition includes up to about 7.5% by weight of the pyrethroid, e.g., permethrin, e.g., between about 2.5% and about 7.5% by weight permethrin, e.g., about 5% by weight permethrin. In certain embodiments, the composition includes about 1%, about 2%, about 3%, about 4%, about 5%, about 6%, about 7%, about 8%, about 9%, or about 10% by weight permethrin. In certain embodiments, the composition includes about 5% by weight permethrin. In certain embodiments permethrin is a mixture of Cis and trans isomer in a ratio of 25:75.

Viscosity-Building Agent

In certain embodiments, a composition of the invention includes a viscosity building agent. As used herein, the term "viscosity building agent" refers to a compound, or combination of compounds, which thickens, or increases the viscosity of a liquid or solution without substantially altering its other properties. Viscosity building agents are also known as "thickeners". The terms "viscosity building agent" and "thickener" are synonymous and are used interchangeably herein. In certain embodiments, a viscosity building agent may improve the suspension of other ingredients or emulsions, or increase the stability of a composition. Exemplary viscosity building agents include a carbomer (e.g., carbomer homopolymer type B), xanthan gum, carboxymethyl cellulose, hydroxymethyl cellulose, hydroxyethyl cellulose, hydroxypropyl cellulose, magnesium aluminum silicate, polaxamer, acrylamide/sodium acryloydimethylaurate copolymer, polyvinylpyrrolidone, and natural gums. In certain embodiments, inclusion of viscosity building agent will alter the spray pattern of the composition.

In certain embodiments, a composition of the invention includes between about 0.1% and about 0.3% by weight of the viscosity building agent. For example, in certain embodiments, the composition comprises between about 0.1% and about 0.3%, between about 0.1% and about 0.25%, between about 0.1% and about 0.2%, between about 0.1% and about 0.15%, between about 0.15% and about 0.3%, between about 0.15% and about 0.25%, between about 0.15% and about 0.2%, between about 0.2% and about 0.3%, between about 0.2% and about 0.25%, or between about 0.25% and about 0.3% by weight of the viscosity building agent In certain embodiments, the viscosity building agent is a carbomer, xanthan gum, or a combination thereof. In certain embodiments, the composition includes a carbomer. For example, in certain embodiments, the composition includes between about 0.01% and about 2.0% by weight of the carbomer, e.g., between about 0.01% and about 1.0%, between about 0.01% and about 0.5%, between about 0.01% and about 0.1%, between about 0.01% and about 0.05%, between about 0.05% and about 1.0%, between about 0.05% and about 0.5%, between about 0.05% and about 0.1%, between about 0.1% and about 1.0%, between about 0.1% and about 0.5%, or between about 0.5% and about 1.0% by weight of the carbomer. For example, in certain embodiments, the composition includes about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, or about 1.0% by weight of the carbomer. In certain embodiments, the composition includes about 0.5% by weight of the carbomer.

In certain embodiments, the composition includes xanthan gum. For example, in certain embodiments, the composition includes between about 0.005% and about 1.0% by weight xanthan gum, e.g., between about 0.005% and about 3.0%, between about 0.005% and about 0.5%, between about 0.005% and about 0.1%, between about 0.005% and about 0.05%, between about 0.005% and about 0.01%, between about 0.01% and about 1.0%, between about 0.01% and about 0.5%, between about 0.01% and about 0.1%, between about 0.01% and about 0.05%, between about 0.05% and about 1.0%, between about 0.05% and about 0.5%, between about 0.05% and about 0.1%, between about 0.1% and about 1.0%, between about 0.1% and about 0.5%, or between about 0.5% and about 1.0% by weight xanthan gum. In certain embodiments, the composition includes about 0.005%, about 0.01%, about 0.05%, about 0.1%, about 0.5%, or about 1% by weight xanthan gum.

In certain embodiments, the viscosity building agent is a carbomer. In certain embodiments, the viscosity building agent is a combination of a carbomer and xanthan gum. In certain embodiments, the composition includes about 0.2% by weight of the carbomer. In certain embodiments, the composition includes about 0.1% by weight xanthan gum. In certain embodiments, the composition includes about 0.2% by weight of both xanthan gum and a carbomer combined.

Emollient

In certain embodiments, a composition of the invention comprises an emollient. As used herein, the term "emollient" refers to compounds that are primarily employed for their skin softening and smoothing properties by providing a barrier to water loss from the skin, and can also be used to adjust the consistency and appearance of a composition. Exemplary emollients include $C_{12}$-$C_{15}$ alkyl benzoate, diisopropyl adipate (also known as isopropyl adipate; adipic acid, diisopropyl ester, hexanedioic acid, bis(1-methylethyl) ester, and DIPA), silicon oil, mineral oil, octisalate, isostearic acid, isopropyl palmitate, isopropyl myristate, oleyl alchol, hydrogenated palm glycerides, dimethyl isosorbide, ethylhexyl stearate, cyclmethicone, dimethicone, lecithin, caprylic/capric triglyceride, lanolin alcohol, acetylated lanolin alcohol, squalene, diethyl sebacate, cetyl palmitate, octyldodecanol, cetearyl ethylhexanoate, caprylic/capric/stearic triglyceride, and isosteric isosterate. In certain embodiments, the emollient includes $C_{12}$-$C_{15}$ alkyl benzoate, diisopropyl adipate, silicon oil, mineral oil, or any combination thereof. In certain embodiments, the emollient is a combination of diisopropyl adipate, silicon oil, and mineral oil.

In certain embodiments, a composition of the invention includes between about 1% and about 60% by weight of the emollient. For example, in certain embodiments, the composition comprises between about 10% and about 25%, between about 10% and about 20%, between about 10% and about 15%, between about 15% and about 25%, between about 15% and about 20%, or between about 20% and about 25%, by weight of the emollient. In certain embodiments, the composition comprises about 10%, about 15%, about 20%, or about 25% by weight of the emollient.

In certain embodiments, the emollient includes diisopropyl adipate. For example, the composition may include between about 0.1% and about 30% by weight diisopropyl adipate, e.g., between about 0.1% and about 20%, between about 0.1% and about 15%, between about 0.1% and about 10%, between about 0.1% and about 7.5%, between about 0.1% and about 5%, between about 0.1% and about 2.5%, between about 0.1% and about 1.0%, between about 0.1% and about 0.5%, between about 0.5% and about 20%, between about 0.5% and about 15%, between about 0.5% and about 10%, between about 0.5% and about 7.5%, between about 0.5% and about 5%, between about 0.5% and about 2.5%, between about 0.5% and about 1.0%, between about 1.0% and about 20%, between about 1.0% and about 15%, between about 1.0% and about 10%, between about 1.0% and about 7.5%, between about 1.0% and about 5%, between about 1.0% and about 2.5%, between about 2.5% and about 20%, between about 2.5% and about 15%, between about 2.5% and about 10%, between about 2.5% and about 7.5%, between about 2.5% and about 5%, between about 5% and about 20%, between about 5% and about 15%, between about 5% and about 10%, between about 5% and about 7.5%, between about 7.5% and about 20%, between about 7.5% and about 15%, between about 7.5% and about 10%, between about 10% and about 20%, between about 10% and about 15%, or between about 15% and about 20% by weight diisopropyl adipate. In certain embodiments, the composition may include about 0.5%, about 1.0%, about 2.5%, about 5%, about 7.5%, about 10%, about 15%, about 20%, about 25%, or about 30% by weight diisopropyl adipate. In certain embodiments, the composition includes about 0.5%, about 5%, or about 10% by weight diisopropyl adipate. In certain embodiments, the composition includes about 5% by weight diisopropyl adipate.

In certain embodiments, the emollient includes a silicon oil. Examples of silicon oil include silicone oil, volatile silicon oil, and cyclomethicone. For example in certain embodiments composition may include a silicon oil, e.g., a volatile silicon oil, e.g., cyclomethicone. For example, the composition may include between about 0.1% and about 20% by weight silicon oil, e.g., between about 0.1% and about 60%, between about 0.1% and about 15%, between about 0.1% and about 10%, between about 0.1% and about 7.5%, between about 0.1% and about 5%, between about 0.1% and about 2.5%, between about 0.1% and about 1.0%, between about 0.1% and about 0.5%, between about 0.5% and about 20%, between about 0.5% and about 15%, between about 0.5% and about 10%, between about 0.5% and about 7.5%, between about 0.5% and about 5%, between about 0.5% and about 2.5%, between about 0.5% and about 1.0%, between about 1.0% and about 20%, between about 1.0% and about 15%, between about 1.0% and about 10%, between about 1.0% and about 7.5%, between about 1.0% and about 5%, between about 1.0% and about 2.5%, between about 2.5% and about 20%, between about 2.5% and about 15%, between about 2.5% and about 10%, between about 2.5% and about 7.5%, between about 2.5% and about 5%, between about 5% and about 20%, between about 5% and about 15%, between about 5% and about 10%, between about 5% and about 7.5%, between about 7.5% and about 20%, between about 7.5% and about 15%, between about 7.5% and about 10%, between about 10% and about 20%, between about 10% and about 15%, or between about 15% and about 20% by weight silicon oil. In certain embodiments, the composition may include about 0.5%, about 1.0%, about 2.5%, about 5%, about 7.5%, about 10%, about 15% or about 20% by weight silicon oil. In certain embodiments, the composition includes between about 0.5% and about 10% by weight silicon oil. In certain embodiments, the composition includes about 0.5%, about 5%, or about 10% by weight silicon oil. In certain embodiments, the composition includes about 5% by weight silicon oil. In certain embodiments, the composition includes about 10% by weight silicon oil. In certain embodiments, the composition includes about 20% by weight silicon oil. In certain embodiments, the composition includes about 30% by weight silicon oil. In certain embodiments, the composition includes about 40% by weight silicon oil. In certain embodiments, the composition includes about 50% by weight silicon oil. In certain embodiments, the composition includes about 60% by weight silicon oil.

In certain embodiments, the emollient includes mineral oil. For example, the composition may include between about 0.1% and about 60% by weight mineral oil, e.g., between about 0.1% and about 20%, between about 0.1% and about 15%, between about 0.1% and about 10%, between about 0.1% and about 7.5%, between about 0.1% and about 5%, between about 0.1% and about 2.5%, between about 0.1% and about 1.0%, between about 0.1% and about 0.5%, between about 0.5% and about 20%, between about 0.5% and about 15%, between about 0.5% and about 10%, between about 0.5% and about 7.5%, between about 0.5% and about 5%, between about 0.5% and about 2.5%, between about 0.5% and about 1.0%, between about 1.0% and about 20%, between about 1.0% and about 15%, between about 1.0% and about 10%, between about 1.0% and about 7.5%, between about 1.0% and about 5%, between about 1.0% and about 2.5%, between about 2.5% and about 20%, between about 2.5% and about 15%, between about 2.5% and about 10%, between about 2.5% and about 7.5%, between about 2.5% and about 5%, between about 5% and about 20%, between about 5% and about 15%, between about 5% and about 10%, between about 5% and about 7.5%, between about 7.5% and about 20%, between about 7.5% and about 15%, between about 7.5% and about 10%, between about 10% and about 20%, between about 10% and about 15%, or between about 15% and about 20% by weight mineral oil. In certain embodiments, the composition may include about 0.5%, about 1.0%, about 2.5%, about 5%, about 7.5%, about 10%, about 15% or about 20% by weight mineral oil. In certain embodiments, the composition includes between about 0.5% and about 10% by weight mineral oil. In certain embodiments, the composition includes about 0.5%, about 5%, about 7%, or about 10% by weight mineral oil. In certain embodiments, the composition includes about 5% by weight mineral oil. In certain embodiments, the composition includes about 7% by weight mineral oil. In certain embodiments, the composition includes about 10% by weight mineral oil. In certain embodiments, the composition includes about 20% by weight mineral oil. In certain embodiments, the composition includes about 30% by weight mineral oil. In certain embodiments, the composition includes about 40% by weight mineral oil. In certain embodiments, the composition includes about 50% by weight mineral oil. In certain embodiments, the composition includes about 60% by weight mineral oil.

In certain embodiments, the emollient includes $C_{12}$-$C_{15}$ alkyl benzoate. For example, the composition may include between about 0.1% and about 20% by weight $C_{12}$-$C_{15}$ alkyl benzoate, e.g., between about 0.1% and about 20%, between about 0.1% and about 15%, between about 0.1% and about 10%, between about 0.1% and about 7.5%, between about 0.1% and about 5%, between about 0.1% and about 2.5%, between about 0.1% and about 1.0%, between about 0.1% and about 0.5%, between about 0.5% and about 20%, between about 0.5% and about 15%, between about 0.5% and about 10%, between about 0.5% and about 7.5%, between about 0.5% and about 5%, between about 0.5% and about 2.5%, between about 0.5% and about 1.0%, between about 1.0% and about 20%, between about 1.0% and about 15%, between about 1.0% and about 10%, between about 1.0% and about 7.5%, between about 1.0% and about 5%, between about 1.0% and about 2.5%, between about 2.5% and about 20%, between about 2.5% and about 15%, between about 2.5% and about 10%, between about 2.5% and about 7.5%, between about 2.5% and about 5%, between about 5% and about 20%, between about 5% and about 15%, between about 5% and about 10%, between about 5% and about 7.5%, between about 7.5% and about 20%, between about 7.5% and about 15%, between about 7.5% and about 10%, between about 10% and about 20%, between about 10% and about 15%, or between about 15% and about 20% by weight $C_{12}$-$C_{15}$ alkyl benzoate. In certain embodiments, the composition may include about 0.5%, about 1.0%, about 2.5%, about 5%, about 7.5%, about 10%, about 15% or about 20% by weight $C_{12}$-$C_{15}$ alkyl benzoate. In certain embodiments, the composition includes between about 0.5% and about 10% by weight $C_{12}$-$C_{15}$ alkyl benzoate. In certain embodiments, the composition includes about 0.5%, about 5%, about 7%, or about 10% by weight $C_{12}$-$C_{15}$ alkyl benzoate. In certain embodiments, the composition includes about between about 5% and about 10% by weight $C_{12}$-$C_{15}$ alkyl benzoate.

In certain embodiments, the emollient includes silicon oil and $C_{12}$-$C_{15}$ alkyl benzoate, and the ratio of silicon oil to $C_{12}$-$C_{15}$ alkyl benzoate is between about 10:1 and about 1:20. For example, the ratio of silicon oil to $C_{12}$-$C_{15}$ alkyl benzoate may be between about 1:1 and about 1:10, 1:1, 1:5, or 1:10.

In certain embodiments, the emollient includes silicon oil and diisopropyl adipate, and the ratio of silicon oil to diisopropyl adipate is between about 10:1 and about 1:20. For example, the ratio of silicon oil to diisopropyl adipate may be between about 1:1 and about 1:10, 1:1, 1:5, or 1:10.

Emulsifier/Surfactant

In certain embodiments, a composition of the invention includes a emulsifier/surfactant. As used herein, the term "emulsifier/surfactant" refers to a substance that stabilizes the mixture of oil and water. A surfactant and the emulsifier are the, two terms that are used interchangeably herein, for such substances. Exemplary emulsifiers/surfactants include glycerol fatty acid esters (e.g., glycerol monostearate, e.g., self-emulsifying glyceryl monostearate), PEG40 hydrogenated castor oil, cholesterol, steareth-10, steareth-20, polyoxyethylene (POE) 20 cetyl ether, ceteareth-20, cetostearyl alcohol, cetyl alcohol, sorbitan monolaurete, mono and diglycerides of fatty acid, sorbitan monostearate, sorbitan tristearate, fatty alcohols (e.g., stearyl alcohol), polyoxyethylene 5 glyceryl stearate, glyceryl distearate, polyglyceryl-3-stearate, polyoxyethylene 10 stearyl, cetyl alcohol, ceteth-20, fatty acids (e.g., stearic acid), emulsifying wax, cetearyl alcohol, polyoxyethylene alkyl ethers (e.g., Brij 30,35,52 and polyoxylcetostearyl ether), polyoxyethylene castor oil derivatives (e.g., polyoxyl 35,40,60,100 and 200 hydrogenated castor oil), polyoxyethylene sorbiatn fatty acid esters (e.g., polysorbate 20,40,60 and 80), polyoxyethylene steartes (e.g., polyoxyl 2,4,6,8,12,20,40 and 100 stearate), and PEG-75 stearate.

In certain embodiments, a composition of the invention includes between about 1% and about 10% by weight of the emulsifier/surfactant. For example, in certain embodiments, the composition comprises between about 1% and about 10%, between about 1% and about 7.5%, between about 1% and about 5%, between about 1% and about 2.5%, between about 2.5% and about 10%, between about 2.5% and about 7.5%, between about 2.5% and about 5%, between about 5% and about 10%, between about 5% and about 7.5%, or between about 7.5% and about 10% by weight of the emulsifier/surfactant. In certain embodiments, the composition comprises about 1%, about 2%, about 3%, about 4%, about 5%, about 6%, about 7%, about 8%, about 9%, or about 10% by weight of the emulsifier/surfactant.

In certain embodiments, the emulsifier/surfactant includes glyceryl monostearate, PEG40 hydrogenated castor oil, POE20 cetyl ether, and any combination(s) thereof. In certain embodiments, the emulsifier/surfactant includes glycerol monostearate, PEG40 hydrogenated castor oil, cholesterol, steareth-10, steareth-20, or any combination(s) thereof. In certain embodiments, the emulsifier/surfactant is a combination of glycerol monostearate, PEG40 hydrogenated castor oil, cholesterol, and steareth-10. In certain embodiments, the emulsifier/surfactant is a combination of glycerol monostearate, and PEG40 hydrogenated castor oil.

In certain embodiments, the emulsifier/surfactant includes glycerol monostearate. The composition may include, for example, between about 0.5% and about 10% by weight glycerol monostearate, e.g., between about 0.5% and about 10%, between about 0.5% and about 7.5%, between about 0.5% and about 5%, between about 0.5% and about 2.5%, between about 0.5% and about 1%, between about 1% and about 10%, between about 1% and about 7.5%, between about 1% and about 5%, between about 1% and about 2.5%, between about 2.5% and about 10%, between about 2.5% and about 7.5%, between about 2.5% and about 5%, between about 5% and about 10%, between about 5% and about 7.5%, or between about 7.5% and about 10% by weight glycerol monostearate. In certain embodiments, the composition includes about 0.5%, about 1%, about 2%, about 3%, about 4%, about 5%, about 6%, about 7%, about 8%, about 9%, or about 10% glycerol monostearate. In certain embodiments, the composition includes about 2% glycerol monostearate. In certain embodiments, the composition includes about 3% glycerol monostearate.

In certain embodiments, the emulsifier/surfactant includes PEG40 hydrogenated castor oil. The composition may include, for example, between about 0.1% and about 5% by weight PEG40 hydrogenated castor oil, e.g., between about 0.1% and about 5%, between about 0.1% and about 2.5%, between about 0.1% and about 1%, between about 0.1% and about 0.5%, between about 0.5% and about 5%, between about 0.5% and about 2.5%, between about 0.5% and about 1%, between about 1% and about 5%, between about 1% and about 2.5%, or between about 2.5% and about 5% by weight PEG40 hydrogenated castor oil. In certain embodiments, the composition includes about 0.1%, about 0.25%, about 0.5%, about 0.75%, about 1%, about 2%, about 3%, about 4% or about 5% by weight PEG40 hydrogenated castor oil. In certain embodiments, the composition includes about 1% by weight PEG40 hydrogenated castor oil.

In certain embodiments, the emulsifier/surfactant includes cholesterol. The composition may include, for example, between about 0.1% and about 5% by weight cholesterol, e.g., between about 0.1% and about 5%, between about 0.1% and about 2.5%, between about 0.1% and about 1%, between about 0.1% and about 0.5%, between about 0.5% and about 5%, between about 0.5% and about 2.5%, between about 0.5% and about 1%, between about 1% and about 5%, between about 1% and about 2.5%, or between about 2.5% and about 5% by weight cholesterol. In certain embodiments, the composition includes about 0.1%, about 0.25%, about 0.5%, about 0.75%, about 1%, about 2%, about 3%, about 4% or about 5% by weight cholesterol. In certain embodiments, the composition includes about 1% by weight cholesterol.

In certain embodiments, the emulsifier/surfactant includes steareth-10. The composition may include, for example, between about 0.1% and about 5% by weight steareth-10, e.g., between about 0.1% and about 5%, between about 0.1% and about 2.5%, between about 0.1% and about 1%, between about 0.1% and about 0.5%, between about 0.5% and about 5%, between about 0.5% and about 2.5%, between about 0.5% and about 1%, between about 1% and about 5%, between about 1% and about 2.5%, or between about 2.5% and about 5% by weight steareth-10. In certain embodiments, the composition includes about 0.1%, about 0.25%, about 0.5%, about 0.75%, about 1%, about 2%, about 3%, about 4% or about 5% by weight steareth-10. In certain embodiments, the composition includes about 1% by weight steareth-10.

In certain embodiments, the emulsifier/surfactant includes steareth-20. The composition may include, for example, between about 0.1% and about 5% by weight steareth-20, e.g., between about 0.1% and about 5%, between about 0.1% and about 2.5%, between about 0.1% and about 1%, between about 0.1% and about 0.5%, between about 0.5% and about 5%, between about 0.5% and about 2.5%, between about 0.5% and about 1%, between about 1% and about 5%, between about 1% and about 2.5%, or between about 2.5% and about 5% by weight steareth-20. In certain embodiments, the composition includes about 0.1%, about 0.25%, about 0.5%, about 0.75%, about 1%, about 2%, about 3%, about 4% or about 5% by weight steareth-20. In certain embodiments, the composition includes about 1% by weight steareth-20.

Humectant

In certain embodiments, a composition of the invention comprises a humectant. Exemplary humectants include propylene glycol, glycerin, sodium hylauronate, allantoin, butylene glycol, salts of lactic acid, propylene glycol, glyerine, and diethylene glycol. In certain embodiments, the humectant comprises propylene glycol, glycerin or a combination thereof. In certain embodiments, the humectant is propylene glycol. In certain embodiments, the humectant is glycerin.

In certain embodiments, the composition may include, for example, between about 0.5% and about 20% by weight of the humectant, e.g., between about 0.5% and about 10%, between about 0.5% and about 7.5%, between about 0.5% and about 5%, between about 0.5% and about 2.5%, between about 0.5% and about 1%, between about 1% and about 10%, between about 1% and about 7.5%, between about 1% and about 5%, between about 1% and about 2.5%, between about 2.5% and about 10%, between about 2.5% and about 7.5%, between about 2.5% and about 5%, between about 5% and about 10%, between about 5% and about 7.5%, or between about 7.5% and about 10% by weight of the humectant. In certain embodiments, the composition includes about 0.5%, about 1%, about 2%, about 3%, about 4%, about 5%, about 6%, about 7%, about 8%, about 9%, or about 10% by weight of the humectant.

In certain embodiments, the humectant includes propylene glycol. The composition may include, for example, between about 0.5% and about 20% by weight propylene glycol, e.g., between about 0.5% and about 10%, between about 0.5% and about 7.5%, between about 0.5% and about 5%, between about 0.5% and about 2.5%, between about 0.5% and about 1%, between about 1% and about 10%, between about 1% and about 7.5%, between about 1% and about 5%, between about 1% and about 2.5%, between about 2.5% and about 10%, between about 2.5% and about 7.5%, between about 2.5% and about 5%, between about 5% and about 10%, between about 5% and about 7.5%, or between about 7.5% and about 10% by weight propylene glycol. In certain embodiments, the composition includes about 0.5%, about 1%, about 2%, about 3%, about 4%, about 5%, about 6%, about 7%, about 8%, about 9%, or about 10% by weight propylene glycol. In certain embodiments, the composition includes about 3% propylene glycol.

In certain embodiments, the humectant includes glycerin. The composition may include, for example, between about 0.5% and about 20% by weight glycerin, e.g., between about 0.5% and about 10%, between about 0.5% and about 7.5%, between about 0.5% and about 5%, between about 0.5% and about 2.5%, between about 0.5% and about 1%, between about 1% and about 10%, between about 1% and about 7.5%, between about 1% and about 5%, between about 1% and about 2.5%, between about 2.5% and about 10%, between about 2.5% and about 7.5%, between about 2.5% and about 5%, between about 5% and about 10%, between about 5% and about 7.5%, or between about 7.5% and about 10% by weight glycerin. In certain embodiments, the composition includes about 0.5%, about 1%, about 2%, about 3%, about 4%, about 5%, about 6%, about 7%, about 8%, about 9%, or about 10% by weight glycerin. In certain embodiments, the composition includes about 3% glycerin.

Antioxidant

In certain embodiments, a composition of the invention comprises an antioxidant. Exemplary antioxidants include butylated hydroxytoluene (BHT), DL-α-tocopherol, propyl gallate, tertiary butylhydroquinone (tBHQ), butylated hydroxyanisole (BHA), sodium sulphite, N-acetylcysteine, ascorbic acid, edetic acid, sodium edetate, L-cysteine, sodium metabisulfite, glutathione, cysteine, captopril, N-acetyl cysteine, gluthatione, Na-ascorbate, L-cysteine, $Na_2$-EDTA, $Na_2$-EDTA-Ca, methimazole, quercetin, arbutin, aloesin, N-acetylglucoseamine, α-tocopheryl ferulate, MAP (Mg ascorbyl phosphate), sodium benzoate, L-phenylalanine, DMSA (succimer), DPA (D-penicillamine), trientine-HCl, dimercaprol, clioquinol, sodium thiosulfate, TETA, TEPA, curcumin, neocuproine, tannin, cuprizone, sodium hydrogen sulfite, lipoic acid, CB4, CB3, AD4, AD6, AD7, Vitamine E, di-tert-butyl methyl phenols, tert-butylmethoxyphenols, polyphenols, tocopherols, ubiquinones, and caffeic acid.

In certain embodiments, the composition includes, for example, between about 0.01% and about 0.5% by weight of the antioxidant, e.g., between about 0.01% and about 0.5%, between about 0.01% and about 0.1%, between about 0.01% and about 0.075%, between about 0.01% and about 0.05%, between about 0.01% and about 0.025%, between about 0.025% and about 0.5%, between about 0.025% and about 0.1%, between about 0.025% and about 0.075%, between about 0.05% and about 0.05%, between about 0.05% and about 0.5%, between about 0.05% and about 0.1%, between about 0.05% and about 0.075%, between about 0.05% and about 0.05%, between about 0.075% and about 0.5%, between about 0.075% and about 0.1%, or between about 0.1% and about 0.5% by weight of the antioxidant. In certain embodiments, the composition includes about 0.01%, about 0.025%, about 0.05%, about 0.075%, about 0.1%, or about 0.5% by weight of the antioxidant.

In certain embodiments, the antioxidant includes butylated hydroxytoluene (BHT). The composition may include, for example, between about 0.01% and about 0.5% by weight butylated hydroxytoluene (BHT), e.g., between about 0.01% and about 0.5%, between about 0.01% and about 0.1%, between about 0.01% and about 0.075%, between about 0.01% and about 0.05%, between about 0.01% and about 0.025%, between about 0.025% and about 0.5%, between about 0.025% and about 0.1%, between about 0.025% and about 0.075%, between about 0.05% and about 0.05%, between about 0.05% and about 0.5%, between about 0.05% and about 0.1%, between about 0.05% and about 0.075%, between about 0.05% and about 0.05%, between about 0.075% and about 0.5%, between about 0.075% and about 0.1%, or between about 0.1% and about 0.5% by weight butylated hydroxytoluene (BHT). In certain embodiments, the composition includes about 0.01%, about 0.025%, about 0.05%, about 0.075%, about 0.1%, or about 0.5% by weight butylated hydroxytoluene (BHT). In certain embodiments, the composition includes about 0.05% by weight butylated hydroxytoluene (BHT).

pH-Adjustment Agent

In certain embodiments, a composition of the invention comprises a pH-adjustment agent. Exemplary pH-adjustment agents include sodium hydroxide, trolamine, hydrocholoric acid, ammonium hydroxide, and potassium hydroxide.

In certain embodiments, the composition may include, for example, between about 0.01% and about 1.0% by weight of the pH-adjustment agent, e.g., between about 0.01% and about 1.0%, between about 0.01% and about 0.5%, between about 0.01% and about 0.2%, between about 0.01% and about 0.1%, between about 0.01% and about 0.05%, between about 0.01% and about 0.02%, between about 0.02% and about 1.0%, between about 0.02% and about 0.5%, between about 0.02% and about 0.2%, between about 0.02% and about 0.1%, between about 0.02% and about 0.05%, between about 0.05% and about 1.0%, between about 0.05% and about 0.5%, between about 0.05% and about 0.2%, between about 0.05% and about 0.1%, between about 0.1% and about 1.0%, between about 0.1% and about 0.5%, between about 0.1% and about 0.2%, between about 0.2% and about 1.0%, between about 0.2% and about 0.5%, between about 0.5% or about 1.0% by weight of the pH-adjustment agent. In certain embodiments, the composition includes about 0.01%, about 0.02%, about 0.05%, about 0.1%, about 0.2%, about 0.5%, or about 1.0% by weight of the pH-adjustment agent.

In certain embodiments, the pH-adjustment agent is sodium hydroxide. The composition may include, for example, between about 0.01% and about 3.0% by weight sodium hydroxide, e.g., between about 0.01% and about 1.0%, between about 0.01% and about 0.5%, between about 0.01% and about 0.2%, between about 0.01% and about 0.1%, between about 0.01% and about 0.05%, between about 0.01% and about 0.02%, between about 0.02% and about 1.0%, between about 0.02% and about 0.5%, between about 0.02% and about 0.2%, between about 0.02% and about 0.1%, between about 0.02% and about 0.05%, between about 0.05% and about 1.0%, between about 0.05% and about 0.5%, between about 0.05% and about 0.2%, between about 0.05% and about 0.1%, between about 0.1% and about 1.0%, between about 0.1% and about 0.5%, between about 0.1% and about 0.2%, between about 0.2% and about 1.0%, between about 0.2% and about 0.5%, between about 0.5% or about 1.0% by weight sodium hydroxide. In certain embodiments, the composition includes about 0.01%, about 0.02%, about 0.05%, about 0.1%, about 0.2%, about 0.5%, or about 1.0% by weight sodium hydroxide. In certain embodiments, the composition includes about 0.12% by weight sodium hydroxide. In certain embodiments, the composition includes about 0.2% by weight sodium hydroxide.

Preservative

In certain embodiments, a composition of the invention comprises a preservative. Exemplary preservatives include methyl paraben (e.g., between about 0.02% and about 0.3% by weight methyl paraben), propyl paraben (e.g., between about 0.01% and about 0.3% by weight propyl paraben), butylparaben (e.g., between about 0.02% and about 0.4% butylparaben), sodium methylparaben (e.g., between about 0.02% and about 0.3% by weight sodium methylparaben), sodium ethylparaben (e.g., between about 0.02% and about 0.3% by weight sodium ethylparaben), benzyl alcohol (e.g., between about 0.2% and about 2.0% by weight benzyl alcohol), phenoxyethanol (e.g., between about 0.5% and about 1% by weight phenoxyethanol), choroxylenol (e.g., between about 0.1% and about 0.8% by weight choroxylenol), imidazodinyl urea (e.g., between about 0.03% and about 0.5% by weight imidazodinyl urea), sorbic acid (e.g., between about 0.05% and about 0.2% by weight sorbic acid), sodium benzoate (e.g., between about 0.02% and about 0.3% by weight sodium benzoate), potassium sorbate (e.g., between about 0.1% and about 0.2% by weight potassium sorbate), benzalkonium chloride (e.g., between about 0.02% and about 0.3% by weight benzalkonium chloride), formaldehyde (e.g., between about 0.01% and about 1.2% by weight formaldehyde), and benzoic acid (e.g., between about 0.1% and about 0.2% by weight benzoic acid). In certain embodiments, the preservative comprises methyl paraben, propyl paraben, or a combination thereof. In certain embodiments, the preservative is a combination of methyl paraben and propyl paraben.

In certain embodiments, composition may include, for example, between about 0.01% and about 1.2% by weight of the preservative, e.g., between about 0.01% and about 0.6%, between about 0.01% and about 0.3%, between about 0.01% and about 0.2%, between about 0.01% and about 0.1%, between about 0.01% and about 0.05%, between about 0.05% and about 0.6%, between about 0.05% and about 0.3%, between about 0.05% and about 0.2%, between about 0.05% and about 0.1%, between about 0.1% and about 0.6%, between about 0.1% and about 0.3%, between about 0.1% and about 0.2%, between about 0.2% and about 0.6%, between about 0.2% and about 0.3%, or between about 0.3% and about 0.6% by weight of the preservative. In certain embodiments, the composition includes about 0.01%, about 0.02%, about 0.03%, about 0.04%, about 0.05%, about 0.1%, about 0.2%, about 0.3%, or about 0.6% by weight of the preservative.

In certain embodiments, the preservative is methyl paraben. The composition may include, for example, between about 0.02% and about 0.3% by weight methyl paraben, e.g., between about 0.02% and about 0.3%, between about 0.02% and about 0.2%, between about 0.02% and about 0.1%, between about 0.02% and about 0.05%, between about 0.05% and about 0.3%, between about 0.05% and about 0.2%, between about 0.05% and about 0.1%, between about 0.1% and about 0.3%, between about 0.1% and about 0.2%, or between about 0.2% and about 0.3% by weight methyl paraben. In certain embodiments, the composition includes about 0.02%, about 0.05%, about 0.1%, about 0.2%, or about 0.3% by weight methyl paraben. In certain embodiments, the composition includes about 0.2% by weight methyl paraben.

In certain embodiments, the preservative is propyl paraben. The composition may include, for example, between about 0.01% and about 0.3% by weight propyl paraben, e.g., between about 0.01% and about 0.3%, between about 0.01% and about 0.2%, between about 0.01% and about 0.1%, between about 0.01% and about 0.05%, between about 0.05% and about 0.3%, between about 0.05% and about 0.2%, between about 0.05% and about 0.1%, between about 0.1% and about 0.3%, between about 0.1% and about 0.2%, or between about 0.2% and about 0.3% by weight propyl paraben. In certain embodiments, the composition includes about 0.01%, about 0.02%, about 0.03%, about 0.04%, about 0.05%, about 0.1%, about 0.2%, or about 0.3% by weight propyl paraben. In certain embodiments, the composition includes about 0.02% by weight propyl paraben.

Exemplary Formulations

In certain embodiments of a composition of the invention, the pyrethroid is permethrin; the viscosity building agent is a combination of a carbomer and xanthan gum; the emulsifier/surfactant is a combination of glycerol monostearate, PEG40 hydrogenated castor oil, cholesterol, and steareth-10; and the emollient is a combination of diisopropyl adipate, silicon oil, and mineral oil. In certain embodiments, the pyrethroid is permethrin; the viscosity building agent is a combination of carbomer and xanthan gum; the emulsifier/surfactant is a combination of glycerol monostearate, PEG40 hydrogenated castor oil, cholesterol, and steareth-10; the emollient is a combination of diisopropyl adipate, silicon oil, and mineral oil; the preservative is a combination of methyl paraben and propyl paraben; the humectant is propylene glycol; and the antioxidant is butylated hydroxytoluene.

In certain embodiments of a composition of the invention, the pyrethroid is permethrin; the viscosity building agent is a carbomer; the emulsifier/surfactant is a combination of glycerol monostearate and PEG40 hydrogenated castor oil; and the emollient is a combination of diisopropyl adipate, silicon oil, and mineral oil. In certain embodiments, the pyrethroid is permethrin; the viscosity building agent is a carbomer; the emulsifier/surfactant is a combination of glycerol monostearate and PEG40 hydrogenated castor oil; the emollient is a combination of diisopropyl adipate, silicon oil, and mineral oil; the preservative is a combination of methyl paraben and propyl paraben; the humectant is glycerin; and the antioxidant is butylated hydroxytoluene.

In certain embodiments, a composition of the invention includes:
  permethrin;
  a viscosity building agent selected from the group consisting of carbomer, xanthan gum, and combinations thereof;
  about 0.1% to about 20%, by weight, silicon oil;
  about 2% to about 20%, by weight, $C_{12}$-$C_{15}$ alkyl benzoate; and
  at least 40%, by weight, water,
  wherein the ratio of silicon oil to $C_{12}$-$C_{15}$ alkyl benzoate is between about 10:1 and about 1:20.

In certain embodiments, the composition includes about 5%, by weight, permethrin.

In certain embodiments, a composition of the invention comprises:
  about 5%, by weight permethrin;
  a viscosity building agent selected from the group consisting of carbomer, xanthan gum, and combinations thereof;
  about 0.1 to about 20%, by weight, silicon oil;
  about 2 to about 20%, by weight, $C_{12}$-$C_{15}$ alkyl benzoate; and
  at least 40%, by weight, water,
  wherein the ratio of silicon oil to $C_{12}$-$C_{15}$ alkyl benzoate is between about 10:1 and about 1:20.

In certain embodiments, a composition of the invention includes: about 5% permethrin, about 5% glycerin, about 0.2% carbomer, about 0.2% methyl paraben, about 0.02% propyl paraben, about 7% mineral oil, about 2% glyceryl monostearate, about 0.05% butylated hydroxytoluene, about 5% $C_{12}$-$C_{15}$ alkyl benzoate, about 1% PEG 40 hydrogenated castor oil, about 0.5% silicon oil, sodium hydroxide, and purified water.

In certain embodiments, a composition of the invention includes: about 5% permethrin, about 5% glycerin, about 0.2% carbomer, about 0.1% xanthan gum, about 0.2% methyl paraben, about 0.02% propyl paraben, about 7% mineral oil, about 2% glyceryl monostearate, about 0.05% butylated hydroxytoluene, about 5% POE 20 cetyl ether, about 5% $C_{12}$-$C_{15}$ alkyl benzoate, about 0.5% silicon oil, sodium hydroxide, and purified water.

In certain embodiments, a composition of the invention includes: about 5% permethrin, about 3% glycerin, about 0.2% carbomer, about 0.2% methyl paraben, about 0.02% propyl paraben, about 7% mineral oil, about 2% glyceryl monostearate, about 0.05% butylated hydroxytoluene, about 10% POE 20 cetyl ether, about 5% $C_{12}$-$C_{15}$ alkyl benzoate, about 1% PEG 40 hydrogenated castor oil, about 10% cyclomethicone, sodium hydroxide, and purified water.

In certain embodiments, a composition of the invention includes, by weight: about 5% permethrin; between about .01% and about 1.0% of a carbomer; between about 0.005% and about 3.0% xanthan gum; between about 0.5% and about 10% glycerol monostearate; between about 0.1% and about 5% PEG40 hydrogenated castor oil; between about 0.1% and about 5% cholesterol; between about 0.1% and about 5% steareth-10; between about 0.1% and about 30% diisopropyl adipate; between about 0.1% and about 60% silicon oil; and between about 0.1% and about 60% mineral oil. In certain embodiments, the composition further includes: between about 0.05% and 1% methyl paraben; between about 0.005% and 0.5% propyl paraben; between about 0.5% and 10% propylene glycol; and/or between about 0.01% and 0.5% butylated hydroxytoluene.

In certain embodiments, a composition of the invention includes, by weight: about 5% permethrin; between about 0.01% and about 2.0% of a carbomer; between about 0.5% and about 10% glycerol monostearate; between about 0.1% and about 5% PEG40 hydrogenated castor oil; between about 0.1% and about 30% diisopropyl adipate; between about 0.1% and about 60% silicon oil; and between about 0.1% and about 60% mineral oil. In certain embodiments, the composition further includes: between about 0.05% and 1% methyl paraben; between about 0.005% and 0.5% propyl paraben; between about 0.5% and 10% glycerin; and/or between about 0.01% and 0.5% butylated hydroxytoluene.

In certain embodiments, a composition of the invention is as depicted in Tables 1 and 2 of the Examples herein.

Unit Dosage Form

In another aspect, the invention provides a unit dosage form comprising from about 20 grams to about 40 grams of a composition of the invention. For example, in certain embodiments, the unit dosage form comprises between about 25 grams and about 35 grams, between about 25 grams and about 32.5 grams, between about 25 grams and about 30 grams, between about 25 grams and about 27.5 grams, between about 27.5 grams and about 35 grams, between about 27.5 grams and about 32.5 grams, between about 27.5 grams and about 30 grams, between about 30 grams and about 35 grams, between about 30 grams and about 32.5 grams, or between about 32.5 grams and about 35 grams of the composition. In certain embodiments, the unit dosage form comprises about 25, about 26, about 27, about 28, about 29, about 30, about 31, about 32, about 33, about 34, or about 35 grams of the composition. In certain embodiments, the unit dosage form comprises about 30 grams of the composition.

C. Spray Devices

The invention also provides delivery systems comprising a disclosed pyrethroid, e.g., permethrin, composition. For example, the invention provides a bag-on-valve (BoV) aerosol system comprising a disclosed pyrethroid, e.g., permethrin, composition. A BoV system comprises an aerosol valve and a welded bag, which contains the composition to be dispensed. The welded bag is typically within a container, such as a can, and the space between the bag and the container is filled with a propellant. The pharmaceutical composition in a BoV device does not come in contact with the propellant, which can be compressed air or nitrogen. This inhibits pyrethroid degradation and ensures product integrity. In some embodiments, the BoV aerosol system may include an actuator, a can, an overcap, or combinations thereof.

This technology allows 360° use for self-application to all areas of the body, including difficult to reach areas like the back between the toes, as well as continuous dispensing with no pumping action required. BoV dispensers eject up to 99.7% of the packaged product, which reduces waste of the active ingredient. The dispenser is environmentally safe, easy to use, and highly convenient, which will improve patient compliance.

Accordingly, the invention provides a Bag-on-Valve (BoV) aerosol system comprising an aerosol valve and an attached bag containing a disclosed composition. In certain embodiments, the bag is a laminated aluminum bag. In certain embodiments, the system further comprises a propellant, e.g., compressed air or nitrogen. In certain embodiments, the system further comprises an actuator. In certain embodiments, the system further comprises a container, e.g., can, aluminum plate, or tin plate. In certain embodiments, the system further comprises an overcap.

In certain embodiments, the pressure in the system, for example, between the inner wall of a container and a composition containing bag, is between about 100 psi and about 130 psi, e.g., between about 100 psi and about 130 psi, between about 110 psi and about 130 psi, between about 120 psi and about 130 psi, between about 100 psi and about 120 psi, between about 110 psi and about 130 psi, or between about 100 psi and about 110 psi. In certain embodiments, the pressure in the system is about 100 psi, 110 psi, 120 psi, or 130 psi.

In certain embodiments, the composition has a mean particle diameter of between about 30 µm and about 150 µm, e.g., between about 30 µm and about 150 µm, e.g., between about 30 µm and about 125 µm, e.g., between about 30 µm and about 100 µm, e.g., between about 30 µm and about 90 µm, e.g., between about 30 µm and about 80 µm, e.g., between about 30 µm and about 70 µm, e.g., between about 30 µm and about 60 µm, e.g., between about 30 µm and about 50 µm, e.g., between about 30 µm and about 40 µm, e.g., between about 40 µm and about 150 µm, between about 40 µm and about 125 µm, between about 40 µm and about 100 µm, between about 40 µm and about 100 µm, between about 40 µm and about 90 µm, between about 40 µm and about 80 µm, between about 40 µm and about 70 µm, between about 40 µm and about 60 µm. between about 40 µm and about 50 µm, between about 50 µm and about 150 µm, between about 50 µm and about 125 µm, between about 50 µm and about 100 µm, between about 50 µm and about 90 µm, between about 50 µm and about 80 µm, between about 50 µm and about 70 µm, between about 50 µm and about 60 µm, between about 60 µm and about 150 µm, between about 60 µm and about 125 µm, between about 60 µm and about 100 µm, between about 60 µm and about 90 µm, between about 60 µm and about 80 µm, between about 60 µm and about 70 µm, between about 70 µm and about 150 µm, between about 70 µm and about 125 µm, between about 70 µm and about 100 µm, between about 70 µm and about 90 µm, between about 70 µm and about 80 µm, between about 80 µm and about 150 µm, between about 80 µm and about 125 µm, between about 80 µm and about 100 µm, between about 80 µm and about 90 µm, between about 90 µm and about 150 µm, between about 90 µm and about 125 µm, between about 90 µm and about 100 µm, between about 100 µm and about 150 µm, between about 100 µm and about 125 µm, or between about 125 µm and about 150 µm when sprayed from the BoV system. In certain embodiments, the composition has a mean particle diameter of between about 40 µm and about 1000 µm when sprayed from the BoV system. In certain embodiments, the composition has a mean particle diameter of between about 50 µm and about 90 µm when sprayed from the BoV system. In certain embodiments, the composition has a mean particle diameter of about 40 µm, about 50 µm, about 60 µm, about 70 µm, about 80 µm, about 90 µm, or about 100 µm when sprayed from the BoV system.

The invention also provides a method for a delivering a pyrethroid composition, e.g., a disclosed pyrethroid composition, to a subject in need thereof using a spray device, e.g., a Bag-on-Valve (BoV) aerosol system.

D. Methods of Treatment

The present disclosure also provides a method for treating a topical infestation of an arthropod in a subject in need thereof, the method including administering, e.g., topically administering, to the subject a therapeutically effective amount of a composition of the invention, e.g., a sprayable composition comprising: a pyrethroid; a viscosity building agent; an emulsifier/surfactant; and an emollient. In certain embodiments, the method of treating a topical infestation of an arthropod, e.g., scabies, includes administering, e.g., topically administering with a bag-on-valve (BoV) aerosol system of the present invention, to the subject a therapeutically effective amount of a sprayable pyrethroid composition of the invention, e.g., a pharmaceutical composition that includes a pyrethroid; a viscosity building agent; an emulsifier/surfactant; and an emollient. In certain embodiments, the method of treating a topical infestation of an arthropod, e.g., scabies, includes administering, e.g., topically administering with a bag-on-valve (BoV) aerosol system of the present invention, to the subject a therapeutically effective amount of a sprayable pyrethroid composition of the invention, e.g., a sprayable pharmaceutical composition that includes a pyrethroid, e.g., permethrin; a viscosity building agent; an emulsifier/surfactant; an emollient; a preservative; an antioxidant; a humectant; a pH adjustment agent; and a vehicle.

In certain embodiments, the method of treating a topical infestation of an arthropod, e.g., scabies, includes administering, e.g., topically administering with a bag-on-valve (BoV) aerosol system of the present invention, to the subject a therapeutically effective amount of a sprayable pyrethroid composition of the invention, e.g., a sprayable pharmaceutical composition that includes a pyrethroid, e.g., permethrin, emollients diisopropyl adipate, mineral oil, and/or silicone oil; emulsifiers/surfactants glyceryl monostearate, cholesterol, steareth-10, and/or PEG40 hydrogenated castor oil; humectant propylene glycol, and viscosity building agents carbomer and/or xanthan gum. In certain embodiments, the method of treating a topical infestation of an arthropod, e.g., scabies, includes administering, e.g., topically administering with a bag-on-valve (BoV) aerosol system of the present invention, to the subject a therapeutically effective amount of a pyrethroid composition of the invention, e.g., a pharmaceutical composition that includes a pyrethroid, e.g., permethrin, emollients diisopropyl adipate, mineral oil, and/or silicone oil; emulsifiers/surfactants glyceryl monostearate, and/or PEG40 hydrogenated castor oil; humectant glycerin, and viscosity building agent carbomer.

In certain embodiments, the method of treating a topical infestation of an arthropod, e.g., scabies, includes administering, e.g., topically administering with a bag-on-valve (BoV) aerosol system of the present invention, to the subject a therapeutically effective amount of a sprayable pyrethroid composition of the invention, e.g., a sprayable pharmaceutical composition that includes a pyrethroid selected from allethrin, bifenthrin, cyfluthrin, cypermethrin, cyphenothrin, deltamethrin, esfenvalerate, etofenprox, fenpropathrin, fenvalerate, flucythrinate, flumenthrin, imiprothrin, λ-cyhalothrin, metofluthrin, permethrin, prallethrin, resmethrin, silafluofen, sumithrin, τ-fluvalinate, tefluthrin, tetramethrin, tralomethrin, and transfluthrin.

In certain embodiments, the subject suffers from an infestation by an arthropod, arachnid, or myriapod including, but not limited to, *Sarcoptes scabiei* (itch mite); *Pediculus humanus capitis* (head louse); *Anopheles* spp. and *Aedes* spp. (mosquito); *Periplaneta americana* (American cockroach); *Blatella* spp. (including the German cockroach); *Supella longipalpa* (brown-banded cockroach); *Ctenocephalides* spp., *Pulex* spp., *Dasypsyllus* spp., *Nosopsyllus* spp., and *Xenopsylla* spp. (fleas); *Cimex lectularius* (bed bugs); ants of the family Formicidae; spiders of the order Araneae; *Attagenus unicolor* (black carpet beetle), flies of the order Diptera; centipedes and millipedes; ticks of the superfamily Ixodoidea; wasps and hornets of the family Vespidae; earwigs of the order Dermaptera; termites; crickets of the family Gryllidae; and *Lepisma saccharina* (silverfish). In certain embodiments, the arthropod is *S. scabiei*. In certain embodiments, the arthropod is *P. humanus capitis*. In certain embodiments, the arthropod is *S. scabiei* and the pyrethroid is permethrin.

Pharmaceutical compositions of the invention can be presented in a dosage unit form and can be prepared by any suitable method. A pharmaceutical composition should be formulated to be compatible with its intended route of administration. Examples of routes of administration are intravenous (IV), intradermal, inhalation, transdermal, topical, transmucosal, intrathecal and rectal administration. A preferred route of administration is topical. For example, in certain embodiments, the composition of the invention is formulated to be compatible with topical administration, such as in the form of a spray, foam, cream, gel, ointment, emulsion, or lotion. In certain embodiments, the composition is delivered by a spray device. Useful formulations can be prepared by methods known in the pharmaceutical art. For example, see Remington's Pharmaceutical Sciences, 18th ed. (Mack Publishing Company, 1990).

Generally, a therapeutically effective amount of a composition of the invention is in the range of about 400 to about 900 mg per kg body weight per day, preferably about 425 to about 850 mg/kg/day, in single or divided doses. Depending on age, species and condition being treated, dosage levels below the lower limit of this range may be suitable. In other cases, still larger doses may be used without harmful side effects. Larger doses may also be divided into several smaller doses, for administration throughout the day. In certain embodiments, a therapeutically effective amount comprises a single dose of 30 grams of the composition. In certain embodiments, a therapeutically effective amount comprises two doses of 30 grams of the composition. In certain embodiments, a therapeutically effective amount comprises three or more doses of 30 grams of the composition. The amount administered will depend on variables such as the type and extent of disease or indication to be treated, the overall health of the patient, the in vivo potency of the antibody, the pharmaceutical formulation, and the route of administration.

In certain embodiments, the method of treating a topical infestation of an arthropod, e.g., scabies, includes administering, e.g., topically administering with a bag-on-valve (BoV) aerosol system, a pyrethroid composition of the present invention placed inside the bag of the BoV, which is dispensed by a propellant (compressed air/nitrogen), filled in the space between bag and the can of the BoV, by squeezing the bag when a spray button is pressed. During administration, the composition that is squeezed out of the BoV generates a continuous/controlled spray pattern. In certain embodiments, the optimal spray pattern of the composition is obtained at a pressure between about 100 psi and about 130 psi. In certain embodiments, the optimal spray pattern is obtained at about 100 psi, 105 psi, about 110 psi, about 115 psi, about 120 psi, about 125 psi, or about 130 psi.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby.

Example 1

Topical Spray Formulations Comprising Permethrin

The present disclosure can be understood as a composition comprising a pyrethroid, such as permethrin. Below are representative examples of the sprayable composition of the present disclosure. These examples are not intended to be limiting in any way.

TABLE 1

| Ingredient (% by weight) | Ex. 1 | Ex. 2 | Ex. 3 | Comp. Ex 1 | Comp. Ex. 2 |
|---|---|---|---|---|---|
| Permethrin | 5 | 5 | 5 | 0 | 0 |
| Glycerin | 5 | 5 | 3 | 3 | 3 |
| Carbomer | 0.2 | 0.2 | 0.2 | 0.2 | 0.2 |
| Xanthan Gum | 0 | 0.1 | 0 | 0 | 0 |
| Methyl Paraben | 0.2 | 0.2 | 0.2 | 0.2 | 0.2 |
| Propyl Paraben | 0.02 | 0.02 | 0.02 | 0.02 | 0.02 |
| Mineral Oil | 7 | 7 | 0 | 5 | 0 |
| Glyceryl monostearate | 2 | 2 | 2 | 2 | 2 |
| Butylated hydroxytoluene | 0.05 | 0.05 | 0.05 | 0.05 | 0.05 |
| POE20 cetyl ether | 0 | 5 | 0 | 0 | 0 |
| $C_{12}$-$C_{15}$ Alkyl benzoate | 5 | 5 | 10 | 10 | 10 |
| PEG40 hydrogenated castor oil | 1 | 0 | 1 | 1 | 1 |
| Silicon oil | 0.5 | 0.5 | 0 | 0 | 0 |
| Cyclomethicone | 0 | 0 | 10 | 2 | 2 |
| Sodium Hydroxide | q.s.* | q.s. | q.s. | q.s. | q.s. |
| Water | q.s. | q.s. | q.s. | q.s. | q.s. |

*q.s.: Quantum satis (abbreviation q.s. or Q.S.) is a Latin term meaning the amount which is enough.

The topical spray formulation may be provided using Bag-On-Valve (BOV) technology. The formulations in Table 1 were prepared essentially as described in Example 2. The amount of sodium hydroxide varied depending upon the adjusted pH required. The amount of water also varied and was added to achieve a final concentration of 100% by weight for each final formulation.

Example 2

Topical Spray Formulations Comprising Permethrin

This example describes the composition and manufacturing of exemplary sprayable permethrin compositions.

Exemplary sprayable permethrin compositions are depicted in Table 2.

TABLE 2

| Ingredient | \multicolumn{6}{c|}{Composition} | Function | Trade name |
|---|---|---|---|---|---|---|---|---|
| | 1 | 2 | 3 | 4 | 5 | 6 | | |
| | \multicolumn{6}{c|}{Concentration (% by weight)} | | |
| Permethrin | 5.0 | 5.0 | 5.0 | 5.0 | 5.0 | 5.0 | Active | NA |
| Glyceryl monostearate | 3.0 | 3.0 | 3.0 | 2.0 | 3.0 | 2.0 | Emulsifier | Imwitor |
| Diisopropyl Adipate | | | 5.0 | | | 5.0 | Emollient | Crodamol DA |
| Butylated Hydroxytoluene | 0.05 | 0.05 | 0.05 | 0.05 | 0.05 | 0.05 | Antioxident | Butylated Hydroxytoluene |
| $C_{12}$-$C_{15}$ alkyl Benzoate | 5.0 | 5.0 | | 10.0 | 5.0 | | Emollient | Crodamol AB |
| Mineral Oil | 5.0 | 5.0 | 7.0 | | 5.0 | 5.0 | Emollient | Daedol |
| Cholesterol | 1.0 | 1.0 | 1.0 | | 1.0 | | Emulsifier | Cholesterol |
| Steareth-10 | 1.0 | 1.0 | 1.0 | | | | Emulsifier | Brij S10 |
| Steareth-20 | | | | | 1.0 | | Emulsifier | Brij S20 |
| PEG 40 Hydrogenated Castor Oil | 0.5 | 1.0 | 1.0 | 1.0 | 1.0 | 1.0 | Emulsifier | Kolliphor RH 40 |
| Silicone Oil | 5.0 | 5.0 | 5.0 | 10 | 5.0 | 10.0 | Emollient | Dow Corning ® ST - Cyclomethicone |
| Methyl Paraben | 0.2 | 0.2 | 0.2 | 0.2 | 0.2 | 0.2 | Preservative | Methylparaben, NF |
| Propyl Paraben | 0.02 | 0.02 | 0.02 | 0.02 | 0.02 | 0.02 | Preservative | Propylparaben, NF |
| Propylene glycol | 3.0 | 3.0 | 3.0 | | 3.0 | | Humectant | Propylene glycol |
| Glycerin | | | | 3.0 | | 3.0 | Humectant | Glycerin 99.7% |
| Carbomer | 0.05 | 0.15 | 0.15 | 0.15 | 0.15 | 0.15 | Viscosity building agent | Carbomer Homopolymer Type B |
| Sodium Hydroxide | 0.12 | 0.20 | 0.20 | 0.20 | 0.20 | 0.20 | pH adjustment agent | Sodium Hydroxide, NF |
| Xanthan Gum | 0.1 | 0.01 | 0.01 | | 0.1 | | Viscosity building agent | Xantural |
| Purified Water | 70.1 | 70.4 | 68.4 | 68.4 | 70.3 | 68.4 | Vehicle | N/A |

The spray permethrin compositions depicted in Tables 1 and 2 were manufactured as follows. In a suitable container, permethrin, glyceryl monostearate, diisopropyl adipate, butylated hydroxytoluene, $C_{12}$-$C_{15}$ alkyl benzoate, mineral oil, cholesterol, steareth-10, steareth-20, and PEG 40 hydrogenated castor oil, when present, were mixed using a Lightnin mixer equipped with suitable shaft and impeller, while heating to 70-75° C. to generate a first mixture.

In a second container, propylene glycol, glycerin and water, when present, were mixed using a Lightnin mixer equipped with suitable shaft and impeller. The mixture was heated to 70-75° C. Methyl and propylparaben were added and dissolved into the mixture. Xanthan gum, when present, was dispersed in the mixture, and mixture was mixed until uniform to generate a second mixture.

In a separate container, carbomer was dispersed in water, and the mixture was heated to 70-75° C. to generate a third mixture.

The first and second mixtures were combined together. The third mixture was then added. The resulting mixture was mixed and homogenized using a Silverson mixer L5MA at 2,000-8,000 rpm for 2 to 15 minutes to achieve a uniform emulsion. The mixture was allowed to cool to 45-50° C. Silicon oil was added to create the final mixture. The mixture was allowed to cool to 25-28° C. and sodium hydroxide was added as needed to reach the desired pH, which may vary from batch-to-batch of a given formulation. Also, the amount of water may vary from batch-to-batch of a given formulation, and is added to achieve a final concentration of 100% by weight for each final formulation. The resulting compositions had a viscosity in the range of 2,000 to 32,000 centipoise (cPs) and a pH in the range of 4.5 to 7.5.

Example 3

Bag-on-Valve (BoV) Aerosol Systems Including Topical Spray Formulations Comprising Permethrin This example describes the filling and testing of exemplary Bag-on-Valve (BoV) aerosol systems including sprayable permethrin compositions.

Exemplary sprayable permethrin compositions, as described in Example 2, were packaged into 30 mL Bag-on-Valve (BoV) aerosol systems. The BoV system included an aerosol valve with a welded laminated bag with a 1" male/female valve to the top of the can. The composition was placed inside the bag while the propellant (compressed air/nitrogen) was filled in the space between the bag and the can (pre-gas pressure). Once the filling of the composition was complete the actuator was placed on the top. The composition can be dispensed by the propellant compressing the bag when the spray button actuator is pressed. The product is squeezed out of the bag by the propellant, which creates a continuous and controlled spray pattern.

The final pressure in the canister can be important in achieving a consistent spray pattern. The final pressure is a combination of a pre-gas pressure and post-pressure after the composition has been filled. The final pressure can be checked through the stem of the valve using a handheld gauge. To test the impact of the final pressure on the expulsion of the composition, several cans were filled at different pressures ranging from 40 to 70 psi and then the composition was added, which increased the pressure surrounding the composition containing bag. The actuator was placed on the canister and spray button was pressed to observe the spray pattern. Pressure below 100 psi showed a poor sprayability, however, pressure between 100-130 psi was found to be optimum to achieve a desirable spray pattern.

The spray pattern from the BOV systems was tested using 3 different types of actuators from different sources. The actuators tested are referred to as A1 (part number VO4.1808 from Coster USA), A2 (part number BOV-A3-30-PP12-GA30-AL-GOGO-GK05 from Aptar), and A3 (part number V04.1806 from Coster USA). The three actuators mainly differ in the diameter of the orifices and depth of the channels in the insert. A1 and A2 created a "fine mist pattern" with uniform particles/droplets in a continuous spraying fashion. This spray pattern is preferred to cover the wider surface area, such as the surface area of the body. A3 created a "jet stream pattern" which was more localized and very large particles/droplets were observed.

The pump performance of the BOV was tested as follows. The initial weights of 10 filled canisters were recorded and then the pump was continuously pressed to empty the product into a beaker. The final weight of the empty canister was recorded to calculate the discharged composition. It was found that the BOV system fully evacuated the composition from the canister, and could achieve consistent dose delivery.

Compositions were packaged in BOV systems and placed in a stability chamber under different conditions. Based on the results, it was found that the composition should be physically and chemically stable for up to ten months.

Example 4

Treatment of Scabies

In this method, subjects suffering from an infestation of scabies (*S. scabiei*) and in need of treatment are identified via observation from a health care provider and/or a laboratory test. Compositions comprising permethrin are administered via a bag on valve spray product all over the skin, from the neck down to the toes, including all skin folds, such as between toes and fingers, or around waist and buttocks. The permethrin formulation will remain on the skin for about 8-14 hours before being washed off. A repeat application may be applied, if appropriate. It is contemplated that the permethrin formulation will effectively treat an infestation of scabies.

Example 5

Treatment of Head Lice

In this method, subjects suffering from infestation of head lice (*P. humanus capitis*) and in need of treatment are identified via observation from a health care provider and/or a laboratory test. Compositions comprising permethrin are administered via a bag on valve spray product to the affected areas. The permethrin formulation will remain in the hair for about 5-15 minutes, or about 10 minutes before being washed off. A repeat application may be applied, if appropriate. It is contemplated that the permethrin formulation will effectively treat an infestation of head lice.

INCORPORATION BY REFERENCE

The entire disclosure of each of the patent and scientific documents referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A sprayable composition comprising:
   between about 2.5% and about 7.5% by weight permethrin;
   between about 0.01% and about 0.2% by weight of a viscosity building agent comprising a carbomer;
   between about 1% and about 10% by weight of an emulsifier/surfactant comprising cholesterol; and
   between about 1% and about 60% by weight of an emollient comprising mineral oil, diisopropyl adipate, and silicon oil.

2. The sprayable composition of claim 1, wherein the composition comprises between about 0.5% and about 10% by weight of the diisopropyl adipate.

3. The sprayable composition of claim 1, wherein the composition comprises between about 0.5% and about 10% by weight of the mineral oil.

4. The sprayable composition of claim 1, wherein the composition comprises about 5% by weight permethrin.

5. The sprayable composition of claim 1, wherein the composition comprises between about 0.1% and about 5% of the cholesterol.

6. The sprayable composition of claim 1, further comprising a preservative, a humectant, an antioxidant, and/or a pH-adjusting agent.

7. The sprayable composition of claim 6, wherein the preservative comprises methyl paraben, propyl paraben, or a combination thereof.

8. The sprayable composition of claim 7, wherein the composition comprises between about 0.02% and about 0.3% by weight of the methyl paraben.

9. The sprayable composition of claim 7, wherein the composition comprises between about 0.01% and about 0.3% by weight of the propyl paraben.

10. The sprayable composition of claim 6, wherein the humectant comprises propylene glycol, glycerin, or a combination thereof.

11. The sprayable composition of claim 10, wherein the composition comprises between about 0.5% and about 10% by weight of the propylene glycol.

12. The sprayable composition of claim 6, wherein the pH adjustment agent is sodium hydroxide.

13. The sprayable composition of claim 12, wherein the composition comprises between about 0.01% and about 3.0% by weight of the sodium hydroxide.

14. The sprayable composition of claim 1, wherein the composition does not comprise a propellant.

15. A method for treating an infestation of an arthropod in a subject in need of such treatment, the method comprising:

topically administering to the subject a therapeutically effective amount of the sprayable composition of claim 1.

16. A Bag-on-Valve (BoV) aerosol system comprising:
an aerosol valve; and
an attached bag containing the sprayable composition of claim 1.

17. A sprayable composition comprising:
about 5% by weight permethrin;
between about 0.1% and about 0.2% by weight of a carbomer;
between about 0.1% and about 5% by weight of a cholesterol;
between about 5% and about 10% by weight of a mineral oil;
between about 2.5% and about 7.5% by weight diisopropyl adipate; and
between about 2.5% and about 7.5% by weight of a silicon oil.

18. The sprayable composition of claim 17, further comprising:
between about 0.02% and about 0.3% by weight methyl paraben;
between about 0.01% and about 0.3% by weight propyl paraben;
between about 1% and about 5% by weight propylene glycol; and
between about 0.01% and about 0.5% by weight butylated hydroxytoluene.

* * * * *